United States Patent
Nelson et al.

(10) Patent No.: US 7,367,340 B2
(45) Date of Patent: May 6, 2008

(54) SYSTEMS AND METHODS FOR MOVING AND/OR RESTRAINING TISSUE IN THE UPPER RESPIRATORY SYSTEM

(75) Inventors: Lionel M. Nelson, Los Altos Hills, CA (US); Ronald G. Lax, Palm City, FL (US); Eric N. Doelling, Sunnyvale, CA (US)

(73) Assignee: Apneon, Inc., Cupertino, CA (US)

( * ) Notice: Subject to any disclaimer, the term of this patent is extended or adjusted under 35 U.S.C. 154(b) by 28 days.

(21) Appl. No.: 11/656,699

(22) Filed: Jan. 23, 2007

(65) Prior Publication Data
US 2007/0119463 A1  May 31, 2007

Related U.S. Application Data

(62) Division of application No. 10/236,455, filed on Sep. 6, 2002, now Pat. No. 7,216,648.

(51) Int. Cl.
*A61F 5/56* (2006.01)
(52) U.S. Cl. .......................... 128/848; 128/859
(58) Field of Classification Search ............... 128/848, 128/859–862; 602/902; 433/6
See application file for complete search history.

(56) References Cited

U.S. PATENT DOCUMENTS

| | | | |
|---|---|---|---|
| 4,304,227 A | 12/1981 | Samelson | |
| 4,871,310 A * | 10/1989 | Vardimon | ............. 433/19 |
| 4,978,323 A | 12/1990 | Freedman | |
| 5,176,618 A * | 1/1993 | Freedman | ............. 600/12 |
| 5,220,918 A | 6/1993 | Heide et al. | |
| 5,373,859 A | 12/1994 | Forney | |
| 5,465,734 A | 11/1995 | Alvarez et al. | |
| 5,649,540 A | 7/1997 | Alvarez et al. | |
| 5,792,067 A | 8/1998 | Karell | |
| RE36,120 E | 3/1999 | Karell | |
| 5,988,171 A | 11/1999 | Sohn | |
| 6,231,496 B1 | 5/2001 | Wilk | |
| 6,244,865 B1 | 6/2001 | Nelson et al. | |
| 6,250,307 B1 | 6/2001 | Conrad et al. | |
| 6,390,096 B1 | 5/2002 | Conrad et al. | |
| 6,401,717 B1 | 6/2002 | Conrad et al. | |
| 6,408,851 B1 * | 6/2002 | Karell | ............. 128/848 |
| 6,415,796 B1 | 7/2002 | Conrad et al. | |
| 6,450,169 B1 | 9/2002 | Conrad et al. | |
| 6,490,885 B1 | 12/2002 | Wilkinson | |
| 6,523,541 B2 | 2/2003 | Knudson | |
| 2001/0047805 A1 | 12/2001 | Scarberry et al. | |

* cited by examiner

*Primary Examiner*—Michael A. Brown
(74) *Attorney, Agent, or Firm*—Ryan, Kromholz & Manion, S.C.

(57) ABSTRACT

Systems and methods selectively stabilize tissue in the oral cavity. The systems and methods implant a first implant element in a bone region within an oral cavity and implant a second implant element in a tongue region within the oral cavity. The systems and methods resist posterior movement of the tongue within the oral cavity by coupling the first implant element to the second implant element within the oral cavity. By coupling, the systems and methods apply force, e.g., tension, between the first and second implant elements.

16 Claims, 28 Drawing Sheets

SYSTEMS AND METHODS FOR MOVING AND/OR RESTRAINING TISSUE IN THE UPPER RESPIRATORY SYSTEM

RELATED APPLICATION

This application is a division of U.S. patent application Ser. No. 10/236,455, filed Sep. 6, 2002 now U.S. Pat. No. 7,216,648, and entitled "Systems and Methods for Moving and/or Restraining Tissue in the Upper Respiratory System."

FIELD OF THE INVENTION

The invention is directed to systems and methods for moving and/or restraining tissue in the upper respiratory system, e.g., for the treatment of sleep-related breathing disorders such as snoring, upper airway resistance syndrome and obstructive sleep apnea.

BACKGROUND OF THE INVENTION

First described in 1965, sleep apnea is a breathing disorder characterized by brief interruptions (10 seconds or more) of breathing during sleep. Sleep apnea is a common but serious, potentially life-threatening condition, affecting as many as 18 million Americans.

There are two types of sleep apnea: central and obstructive. Central sleep apnea, which is relatively rare, occurs when the brain fails to send the appropriate signals to the breathing muscles to initiate respirations, e.g., as a result of brain stem injury or damage. Mechanical ventilation is the only treatment available to ensure continued breathing.

Obstructive sleep apnea (OSA) is far more common. Normally, the muscles of the upper part of the throat keep the airway open to permit air flow into the lungs. When the muscles of the soft palate at the base of the tongue and the uvula (the small fleshy tissue hanging from the center of the back of the throat) relax and sag, the relaxed tissues may vibrate as air flows past the tissues during breathing, resulting in snoring. Snoring affects about half of men and 25 percent of women—most of whom are age 50 or older.

In more serious cases, the airway becomes blocked, making breathing labored and noisy, or even stopping it altogether. In a given night, the number of involuntary breathing pauses or "apneic events" may be as high as 20 to 30 or more per hour. These breathing pauses are almost always accompanied by snoring between apnea episodes, although not everyone who snores has this condition. Sleep apnea can also be characterized by choking sensations.

Lack of air intake into the lungs results in lower levels of oxygen and increased levels of carbon dioxide in the blood. The altered levels of oxygen and carbon dioxide alert the brain to resume breathing and cause arousal. The frequent interruptions of deep, restorative sleep often lead to early morning headaches, excessive daytime sleepiness, depression, irritability, and learning and memory difficulties.

The medical community has become aware of the increased incidence of heart attacks, hypertension and strokes in people with moderate or severe obstructive sleep apnea. It is estimated that up to 50 percent of sleep apnea patients have high blood pressure.

Upon an apneic event, the sleeping person is unable to continue normal respiratory function and the level of oxygen saturation in the blood is reduced. The brain will sense the condition and cause the sleeper to struggle and gasp for air. Breathing will then resume, often followed by continued apneic events. There are potentially damaging effects to the heart and blood vessels due to abrupt compensatory swings in blood pressure. Upon each event, the sleeping person will be partially aroused from sleep, resulting in a greatly reduced quality of sleep and associated daytime fatigue.

Although some apneic events are normal in all persons and mammals, the frequency of blockages will determine the seriousness of the disease and opportunity for health damage. When the incidence of blockage is frequent, corrective action should be taken.

The common method of diagnosing and determining the severity of sleep apnea is polysomnography. Polysomnography is a test that records a variety of body functions during sleep, such as the electrical activity of the brain, eye movement, heart rate, etc.

There are several methods and devices presently available for the treatment of snoring and OSA. There are oral appliances which are designed to displace the mandible (lower jaw) in an anterior (forward) direction by attaching to the upper and lower teeth. The intent is to displace the tongue in an anterior direction, increasing the size of the opening behind the tongue, resulting in an increased airway cross section. These devices have been only partially successful and are not tolerated by a significant percentage of the patients who have them fitted.

Another means of controlling snoring and sleep apnea is the use of a machine that delivers increased air pressure to the nose and mouth of the sleeper. These machines are described as CPAP (Continuous Positive Airway Pressure) machines. They entail wearing of a mask, headgear, and flexible hose which is attached to the air pump. A continuous flow of air at higher than ambient air pressure is forced into the persons' airway, preventing closure of the soft tissue and the resultant apneic event. These devices have also been shown to reduce snoring but not necessarily prevent snoring entirely.

Although effective, the CPAP machine is not widely accepted by the patients. Discomfort, the sound of the air pump, claustrophobia and the stigma of being seen while wearing the mask, headgear, and hose have all been listed as reasons for not continuing use of the CPAP.

Several surgical approaches are used for these afflictions. One is a uvulopalatopharyngoplasty (UPPP) in which tissue at the posterior portion of the soft palate is removed, either by surgical excision or by use of a laser (so-called laser ablation). This is an invasive surgical procedure involving considerable pain in the recovery period, which can be lengthy. Side effects can involve escape of fluids upward into the nasal cavity and increased incidence of bothersome choking events. The long-term success of the UPPP in curing snoring and especially sleep apnea is only approximately 50%.

Other even more involved and invasive surgeries involve tongue reduction in which a section of the tongue is excised to reduce the tongue volume and maxillomandibular advancement in which the upper and lower jaws are severed and repositioned to create increased airway space will improve upon the UPPP success rates. Even more so than the UPPP, these procedures are painful, costly and require long recuperative periods. Absolute assurance of a successful outcome is lacking in these operations, also.

An office-based procedure—called the Somnoplasty® procedure (developed by Somnus Medical Technologies) can be performed using local anesthesia to treat upper-airway obstructions. The procedure uses controlled, low-power radiofrequency energy to create one or several submucosal volumetric lesions in the soft palate. Over a period of 6 to 8 weeks, the lesions are naturally resorbed, reducing tissue volume and stiffening remaining tissue in the desired area.

Other more intrusive treatments such as surgical interventions, i.e. glossectomy (reduction of the size of the tongue 34), genioglossal advancement (pulling the genioglossus muscle in an anterior direction to bring the tongue forward), maxillomandibular advancement (surgical alteration of a portion of the jaw bone and teeth plus the portion of the skull to which the upper teeth are attached) and uvulopalatopharyngoplasty—UPPP (the removal of a portion of the soft palate, either by surgical resection or laser ablation) all permanently modify the anatomy and can affect swallowing, speech and comfort in a negative manner. Other proposed devices, such as implantation of springs and other stiffening devices, can also have an undesired effect on daytime functions.

The need remains for simple, cost-effective devices and methods for reducing or preventing snoring and obstructive sleep apnea.

SUMMARY OF THE INVENTION

The invention provides systems and methods for selectively stabilizing tissue in the oral cavity. The systems and methods restrain movement of more mobile tissue within the oral cavity, e.g., the tongue, toward positions in which snoring and/or sleep apnea events can occur.

According to one aspect of the invention, the systems and methods include a first implant element sized and configured for implantation in a bone region within an oral cavity and a second implant element sized and configured for implantation in a tongue region within the oral cavity. The systems and methods also include a third implant element coupled to the first and second implant elements within the oral cavity. The third implant element is capable of applying force between the first and second implant elements such that the implant, in use, resists posterior movement of the tongue within the oral cavity.

In one embodiment, the first implant element is sized and configured for implantation in a mandible.

In one embodiment, the first implant element is sized and configured for implantation in a hyoid bone.

In one embodiment, the third implant element includes a component that applies force between the first and second implant elements in response to magnetic interaction with another component.

According to another aspect of the invention, the systems and methods, comprise a first implant element sized and configured for implantation in a bone region within an oral cavity and a second implant element sized and configured for implantation in a tongue region within the oral cavity. According to this aspect of the invention, a third implant element is coupled to the first and second implant elements within the oral cavity, which is capable of applying tension between the first and second implant elements such that the implant, in use, resists posterior movement of the tongue within the oral cavity.

In one embodiment, the first implant element is sized and configured for implantation in a mandible.

In one embodiment, the third implant element includes an elongated member that applies the tension.

According to another aspect of the invention, a method implants a first implant element in a bone region within an oral cavity and implants a second implant element in a tongue region within the oral cavity. The method resists posterior movement of the tongue within the oral cavity by coupling the first implant element to the second implant element within the oral cavity.

In one embodiment, the first implant element is implanted in a mandible.

In one embodiment, the first implant element is implanted in a hyoid bone.

According to another aspect of the invention, a method implants a first implant element in a bone region within an oral cavity and implants a second implant element in a tongue region within the oral cavity. The method resists posterior movement of the tongue within the oral cavity by placing into tension a third implant element between the second implant element and the first implant element within the oral cavity.

In one embodiment, the first implant element is implanted in a mandible.

In one embodiment, the third element comprises an elongated member placed into tension between the first and second implant elements.

Other features and advantages of the invention shall be apparent based upon the accompanying description, drawings, and claims.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

I. Anatomy of the Upper Respiratory System

Figure 1:
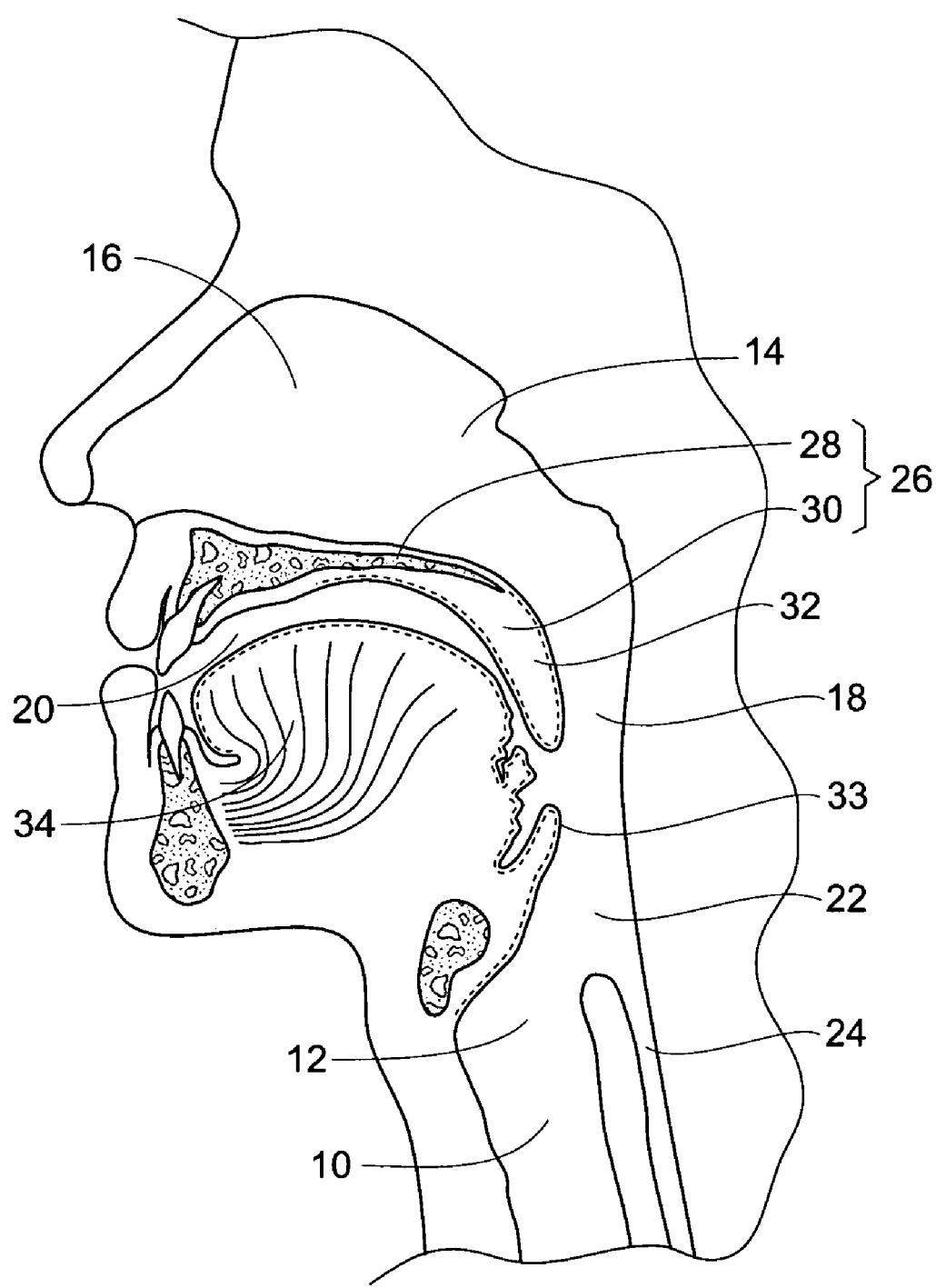
FIG. 1 is an anatomical cross-section of a normal human nasal airway, oral cavity, and oropharynx.

FIG. 1 illustrates the normal anatomy of the human upper respiratory system, which communicates with the trachea 10 and the lower respiratory system through the larynx 12. In humans, the pharynx is divided into nasal, oral, and laryngeal portions. The nasopharynx 14 lies posterior to the nasal cavity 16. The oropharynx 18 communicates with the nasopharynx 14 superiorly, the oral cavity (mouth) 20 anteriorly, and the laryngopharynx 22 inferiorly. The laryngopharynx 22 lies posterior to the larynx 12 and serves as the entrance to the esophagus 24.

The upper part of the oral cavity 20 is the palate 26, and it separates the oral cavity 20 from the nasal cavity 16. The anterior two-thirds of the palate 26 is the bony hard palate 28. The movable posterior third of the palate 26, made up of muscle and aponeurosis, is known as the soft palate 30. The soft palate 30 is suspended from the posterior border of the hard palate 28 and extends posteroinferiorly as a curved free margin from which hangs a conical process, the uvula 32. The tongue 34 is located over the floor of the oral cavity 20. The epiglottis 33 is a thin leaf-shaped structure immediately posterior to the base of the tongue 34. The epiglottis 33 covers the entrance of the larynx 12 when an individual swallows, thereby preventing food or liquids from entering the airway. These structures are all interrelated in the functions of breathing, swallowing and speech.

Figure 2:
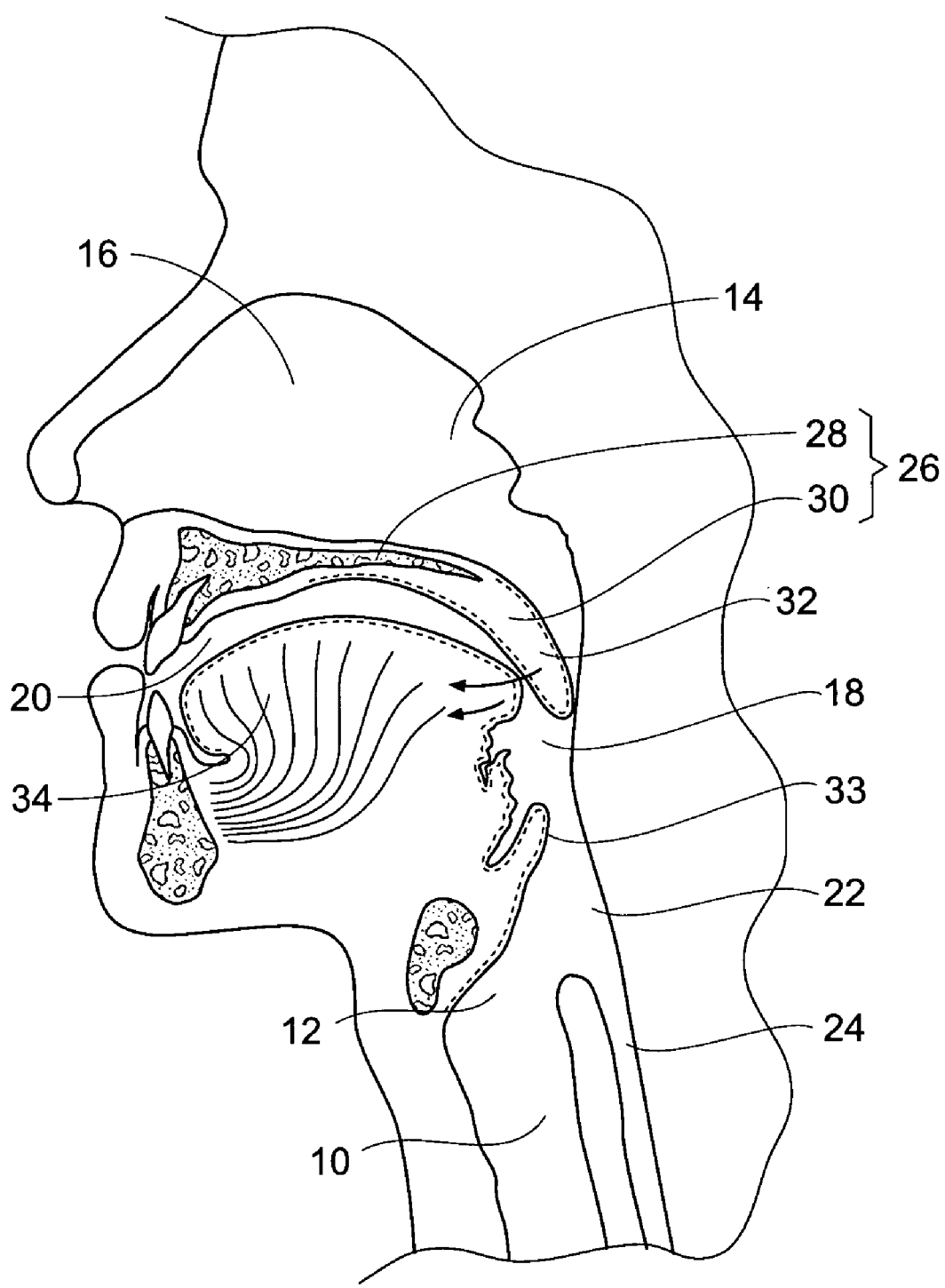
FIG. 2 is a view similar to FIG. 1, illustrating occlusion of the oropharynx that occurs during obstructive sleep apnea.

With reference to FIG. 2, during sleep, the soft palate 30 and uvula 32, being unsupported by bone or cartilage, can droop into the airway and vibrate, resulting in loud snoring. A similar situation exists in which the tongue 34 can become relaxed and move in a posterior direction, partially or fully obstructing the airway. This condition can cause a hypopnea, in which the airway is partially obstructed, making breathing more difficult, or apnea, in which the airway is completely obstructed. Sleep apnea, and to a lesser degree, hypopnea can have extremely serious health consequences.

As FIG. 2 illustrates, the soft palate 30 and uvula 32 may actually come in contact with the posterior wall of the oropharynx 18. In addition, the back of the tongue 34 may come to lie near the posterior wall of the oropharynx 18. Because of the narrowed space, the velocity of the air passing through the airway will be affected and the soft palate 30 can vibrate and/or flutter during respiration, emitting a loud sound (snoring). This can happen with or without the tongue 34 being in the rearward position shown in FIG. 2.

The tongue 34 can also fall toward the rear of the mouth 20 and partially or fully obstruct the airway. At the end of exhalation and the beginning of inhalation is the point at which the tongue 34 and/or soft palate 30 can stop the airflow within the airway, resulting in an apneic event. If the airway is partially obstructed, an hypopnea can occur.

Therefore, as indicated by arrows in FIG. 2, the desirable forces and tissue location are in an anterior direction. If the soft palate 30 and the tongue 34 are moved and retained as shown during sleep, the airway will remain unrestricted and the tendency for the soft palate 30 to vibrate or flutter will be reduced or eliminated entirely.

II. System Overview (Primary Magnet Configured for Anterior Movement of Soft Palate and/or Uvula)

Figure 3A:
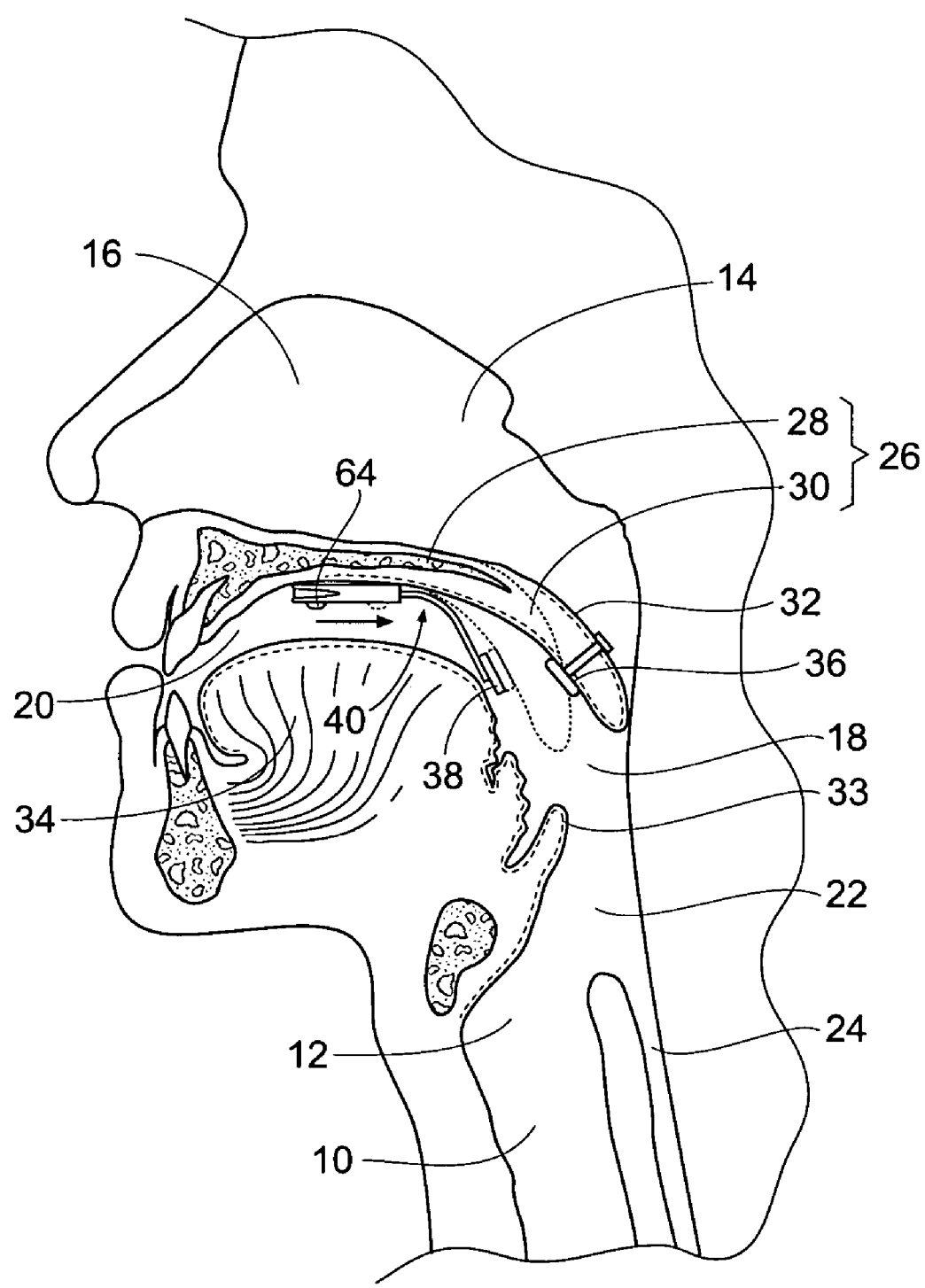
FIG. 3A is an anatomical cross-section of a human nasal airway showing the placement and interaction of primary and secondary magnets, both fixed to surface tissue, to effect anterior movement of the soft palate.
Figure 3B:
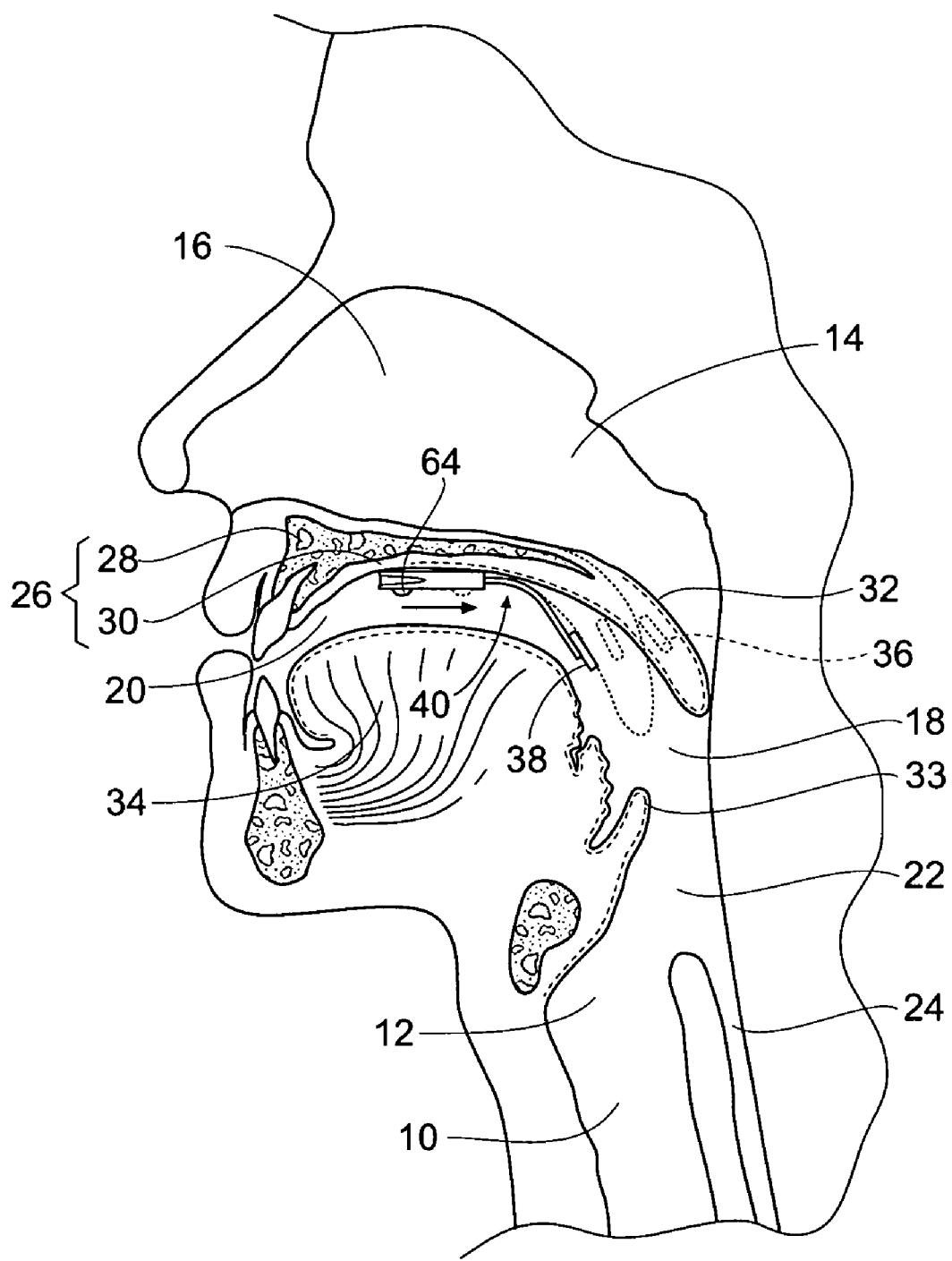
FIG. 3B is an anatomical cross-section of a human nasal airway showing the placement and interaction of a primary magnet implanted in tissue and a secondary magnet affixed to surface tissue to effect anterior movement of the soft palate.

FIGS. 3A and 3B illustrate alternative embodiments of a system for treating sleep-related breathing disorders such as snoring, upper airway resistance syndrome and obstructive sleep apnea. The system employs at least one primary magnet 36 and at least one secondary magnet 38. Together, the magnets 36 and 38 serve to position, stabilize and maintain a preferred orientation of tissue in an oral cavity and airway in both humans and animals. By moving and stabilizing tissue in a desired location and shape, the system mediates or prevents the obstruction of the upper airway that results in sleep-related breathing disorders. Still, as will be described, the system achieves these results without permanent modification of the anatomy.

An object that exhibits magnetic properties (i.e., magnetism) is called a magnet. Magnetism is a force of attraction or repulsion between various substances, especially those made of iron and certain other metals, ultimately due to the motion of electric charges. Every magnet has a magnetic field, which is a region around the magnet in which the magnetic effects are observed. In the illustrated embodiment, the primary and secondary magnets 36 and 38 are desirably permanent magnets, i.e., they maintain an essentially constant magnetic field over time.

The magnets 36 and 38 possess poles of opposite polarity. The poles are centers where magnetic attraction is strongest. If the magnet is free to turn, one pole will point north, and is thus called a North pole, and the opposite pole is likewise called a South pole. According to physical laws, poles of like polarity (North-North or South-South) repel each other with a magnetic force. On the other hand, poles of unlike polarity (North-South or South-North) attract each other with a magnetic force. The force of magnetic attraction or repulsion depends on the strength of the magnets and the distance between the poles.

In the alternative embodiments illustrated in FIGS. 3A and 3B, the primary and secondary magnets 36 and 38 are mutually oriented so that the force of magnetic attraction draws the primary magnet 36 toward the secondary magnet 38. That is, the primary magnet 36 is of opposite polarity from the secondary magnet 38, e.g., the primary magnet 36 is of North polarity and the secondary magnet 38 is of South polarity, or vice versa. In this Specification, such an orientation of magnetic poles is called "complementary."

In this arrangement, the secondary magnet 38 is intended to be carried in or by relatively immobile tissue, or at least mounted more securely than the primary magnet 36. The primary magnet 36 is intended to be carried in or by mobile tissue. Thus, as the more mobile primary magnet 36 is drawn toward the less mobile secondary magnet 38, a desired movement of tissue occurs.

It should be appreciated that either magnet 36 or 38 may exert a magnetic force on a material that is not magnetized. Therefore, one of the magnets 36 or 38 can be replaced by a material, e.g., ferrous plate, on which the remaining magnet 36 or 38 is able to exert an attractive magnetic force. Of course, a ferrous plate could not exert a repelling force without itself being magnetized. The terms "primary magnet(s)" or "secondary magnet(s)" as used in this specification are therefore not limited to an object that exhibits magnetic properties (i.e., an object that is magnetized), but also encompass an object made of a material that is not itself magnetized but which is attracted to another object that is magnetized. Still, use of the terms requires that at least one of the "primary magnet(s)" or "secondary magnet(s)" comprise an object that is magnetized.

In FIGS. 3A and 3B, the primary magnet 36 is carried by more mobile tissue of the soft palate 30, e.g., at the root of the uvula 32. In FIG. 3A, the primary magnet 36 is attached to surface tissue at the root of the uvula 32. In FIG. 3B, the primary magnet 36 is implanted in tissue at the root of the uvula 32. In either situation, the portion(s) of the primary magnet 36 contacting tissue (either surface or subsurface) desirably includes a biocompatible coating to prevent interaction between the magnet and tissues/fluids of the body. The secondary magnet 38 is carried by an oral appliance magnet holder 40, which is carried by less mobile tissue (i.e., the upper teeth) along the roof of the mouth. Technical features of the holder 40 will be described in greater detail later.

Arranged in a complementary manner, the less mobile secondary magnet 38 acts upon the more mobile primary magnet 36 to draw the primary magnet 36, and, with it, the mobile tissue of the soft palate 30, in an anterior direction (depicted by phantom lines in FIG. 3A and FIG. 3B) to prevent obstruction of the airway.

As will be demonstrated, the primary and secondary magnets 36 and 38 can be sized, configured, and placed in a variety of arrangements to effect the desired positioning of tissue. Depending upon the degree of flexibility or firmness of the palate 26, the physician may attach one or several primary magnets 36 to the soft palate 30 and variations in the oral appliance 40 can accommodate the variation in the number and position of the magnets 36.

As will be discussed later, in alternative arrangements, the primary and secondary magnets 36 and 38 may be mutually oriented so that the force of magnetic attraction repels the magnets 36 and 38 away from each other. That is, the primary magnet 36 is of the same polarity from the secondary magnet 38, e.g., the primary and secondary magnets 36 and 38 are both of North polarity or South polarity. In this Specification, such an orientation of magnetic poles is called "non-complementary." In this arrangement, the secondary magnet 38 is still intended to be carried in or by relatively immobile tissue, while the primary magnet 36 is intended to be carried in or by mobile tissue. Thus, the more mobile primary magnet 36 is repelled away from the less mobile secondary magnet 38, and a desired movement of tissue occurs.

A. The Primary Magnet(s)

Figure 4A:
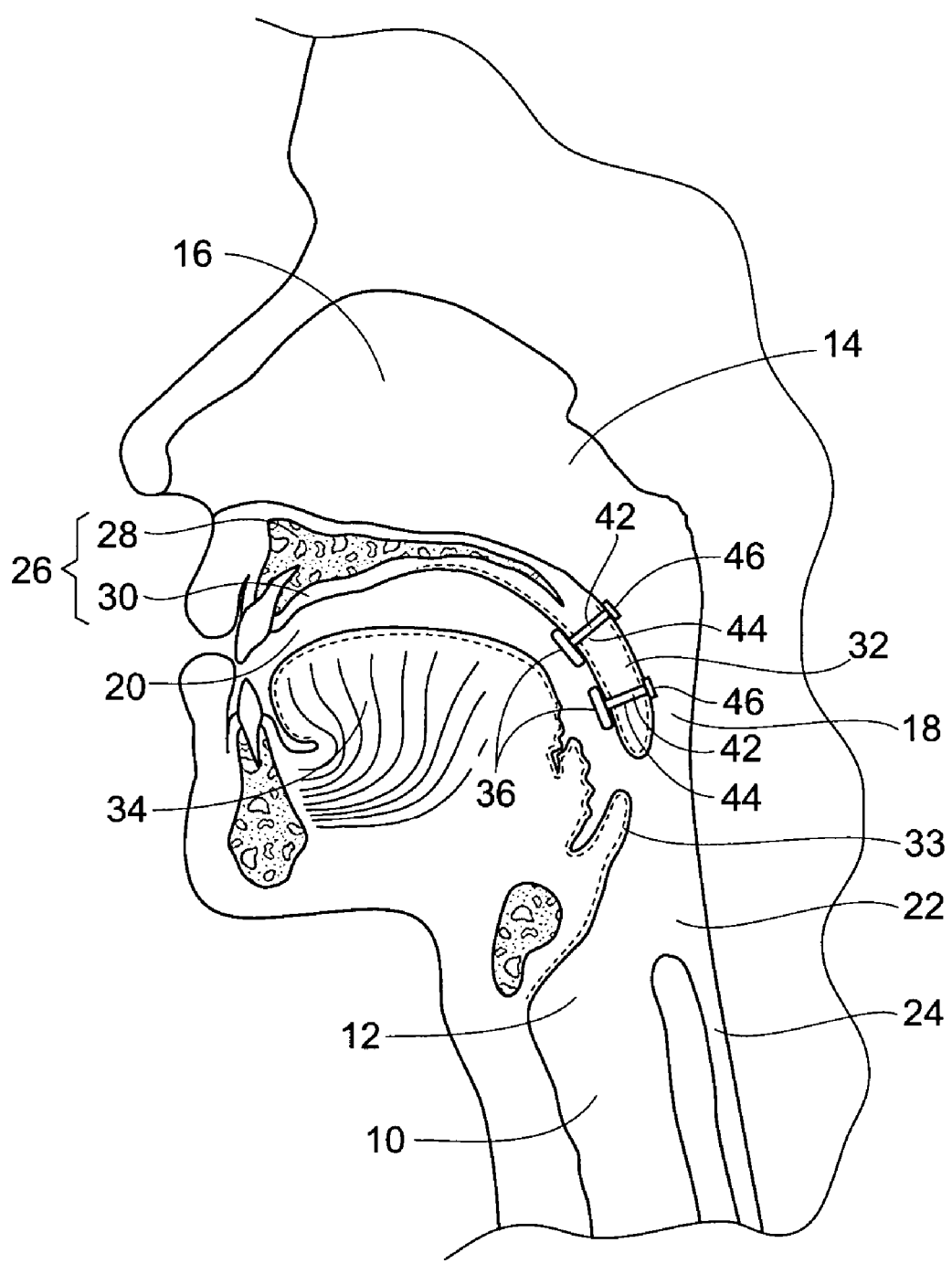
FIG. 4A is an anatomical cross-section of a human nasal airway showing permanent primary magnet locations affixed to surface tissue of the soft palate and uvula.
Figure 4B:
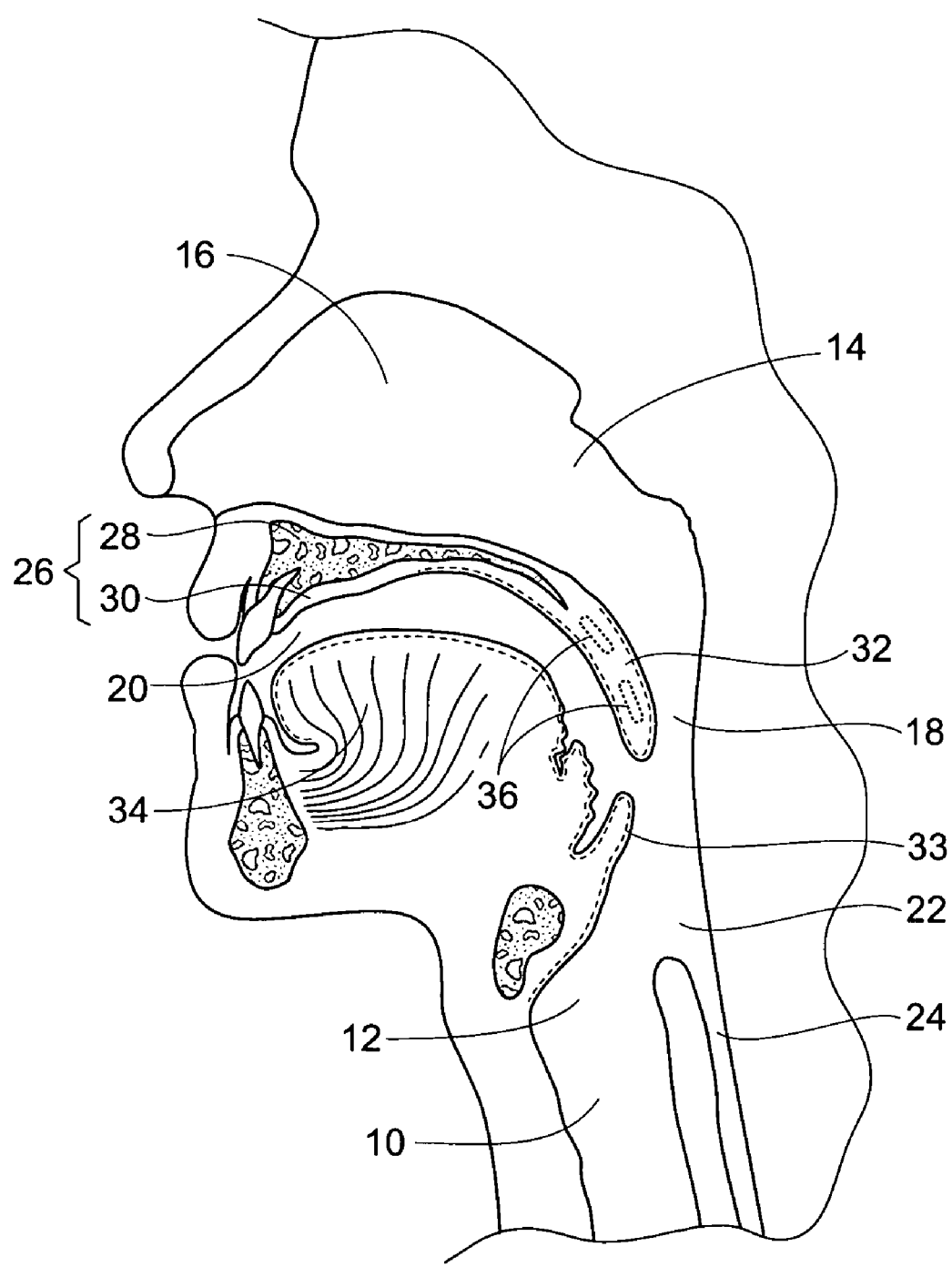
FIG. 4B is an anatomical cross-section of a human nasal airway showing permanent primary magnet locations implanted in tissue of the soft palate and uvula
Figure 14:
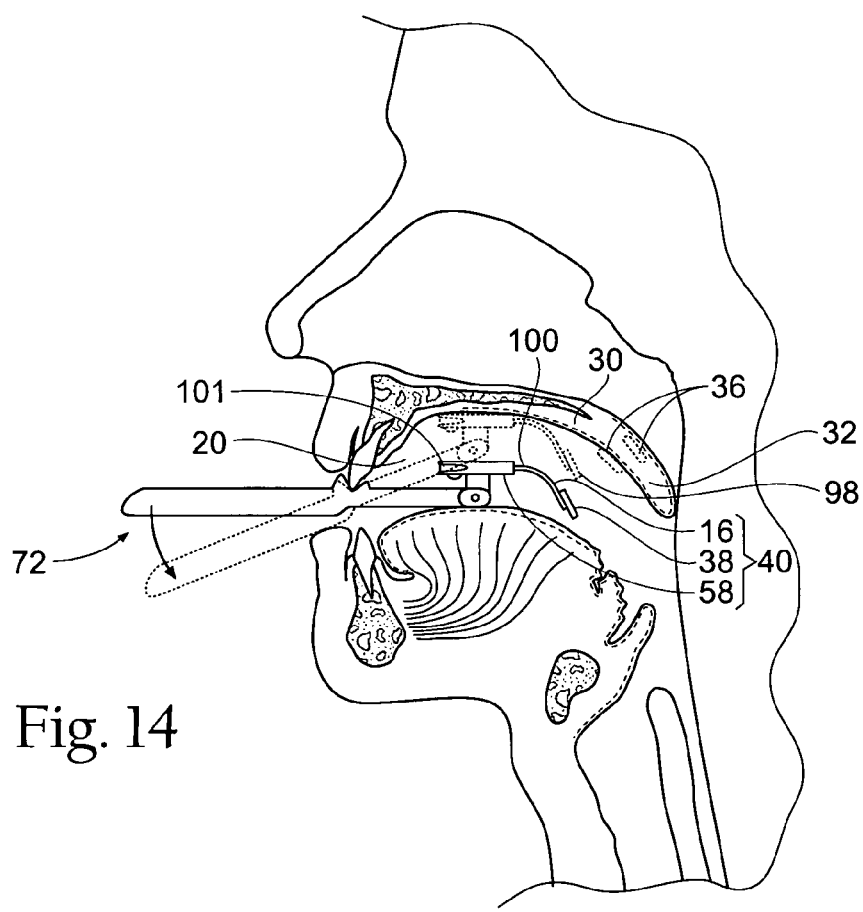
FIG. 14 is an anatomical cross-section of a human upper airway showing the use of a positioning tool to place the oral appliance of FIGS. 7 and 8 within the oral cavity.

FIGS. 4A and 4B show alternatively implementation of a representative embodiment, in which two primary magnets 36 are attached to the anterior surface of the soft palate 30 and root of the uvula 32 respectively. In FIG. 4A, the magnets 36 are removably attached to exterior tissue using studs 42 that are fitted into pierced holes 44 in the tissue and are secured by a retaining lock device, e.g., a backing plate 46 on the posterior surface of the soft palate 30. The backing plate 46 is desirably made of silicone or a similar biocompatible elastomeric material. Alternatively, as seen in FIG. 4B and FIG. 14, the primary magnets 36 may be implanted within the soft palate 30. The portion(s) of the primary magnet 36 contacting tissue (either surface or subsurface) desirably includes a biocompatible coating to prevent interaction between the magnet and tissues/fluids of the body.

Figure 5A:
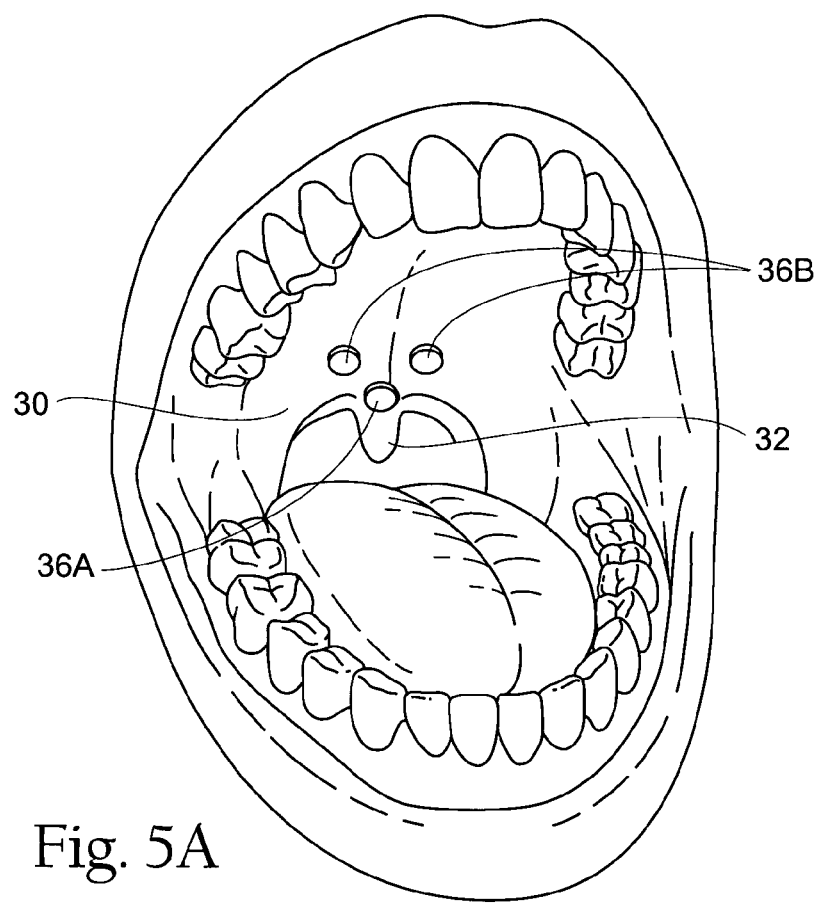
FIG. 5A is an anterior view of a human oral cavity showing placement of permanent primary magnets affixed to surface tissue of the soft palate and at the root of the uvula.
Figure 6A:
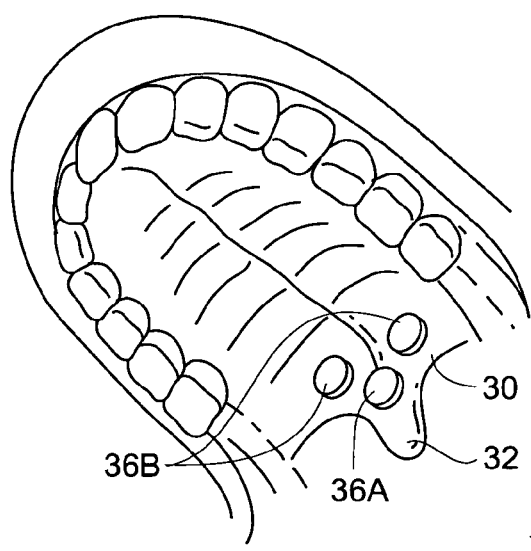
FIG. 6A is an oblique view of the primary magnet locations shown in FIG. 5A.
Figure 5B:
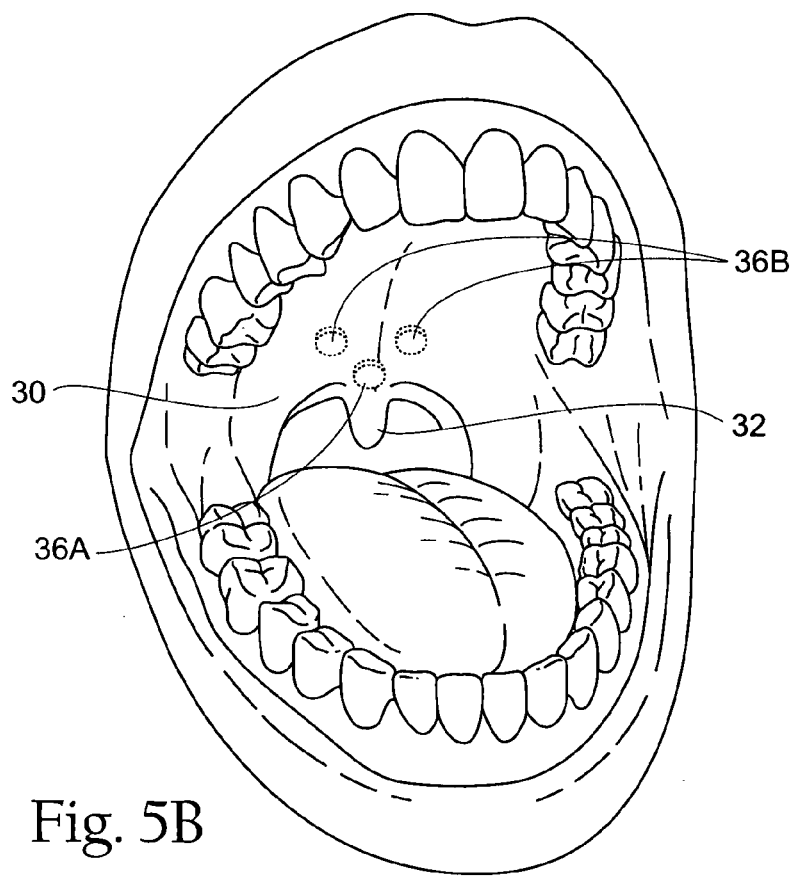
FIG. 5B is an anterior view of a human oral cavity showing placement of permanent primary magnets implanted in tissue of the soft palate and at the root of the uvula.
Figure 6B:
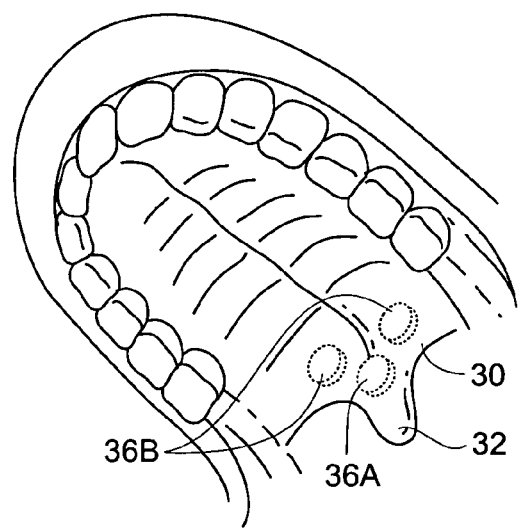
FIG. 6B is an oblique view of the primary magnet locations shown in FIG. 5B.

FIGS. 5A/5B and 6A/6B show alternative arrangements of primary magnets 36 in the soft palate 30. In this arrangement, a primary magnet 36A is attached to the soft palate 30 at approximately the base of the uvula 32. A pair of additional primary magnets 36B are positioned in the soft palate 30 anterior to and radially from the first primary magnet 36A in a triangular configuration. In FIGS. 5A and 6A, the primary magnets 36 are attached to surface tissue at the base of the uvula 32. In FIG. 5B and 6B, the primary magnets 36 are implanted in tissue at the base of the uvula 32. As before stated, the portions of the primary magnets 36 contacting tissue (either surface or subsurface) desirably includes a biocompatible coating to prevent interaction between the magnet and tissues/fluids of the body.

Figure 7:
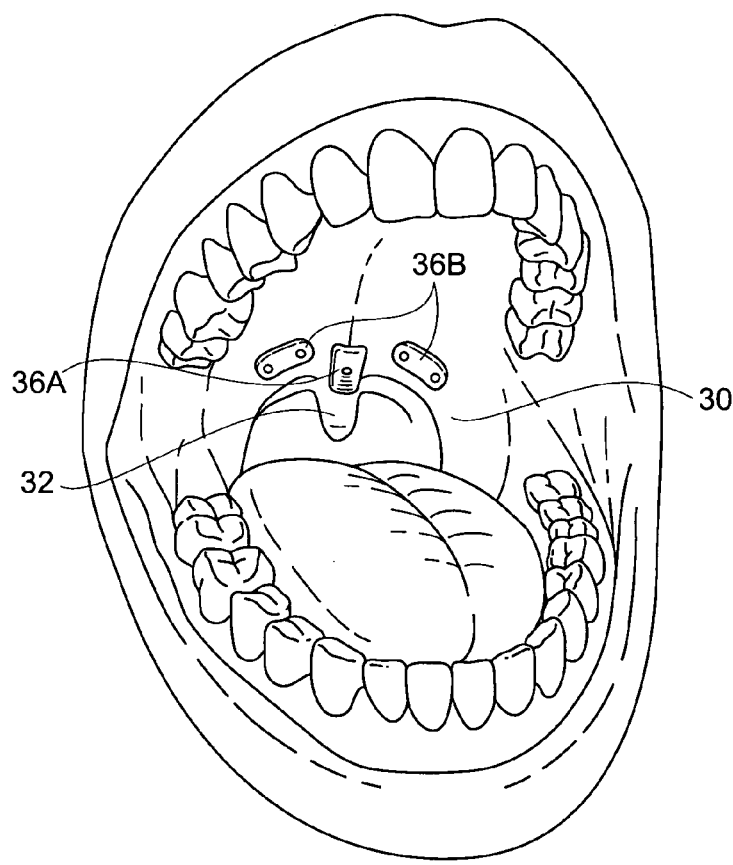
FIG. 7 is an anatomical view of human oral cavity and illustrating the configuration and placement of primary magnets on the uvula and soft palate.

FIGS. 7 to 11 detail representative embodiments of soft palate primary magnets 36A and 36B. FIG. 7 shows a primary magnet 36A configured for attachment to the uvula 32 and primary magnets 36B configured for attachment to the soft palate 30 adjacent the uvula 32.

Figure 8:
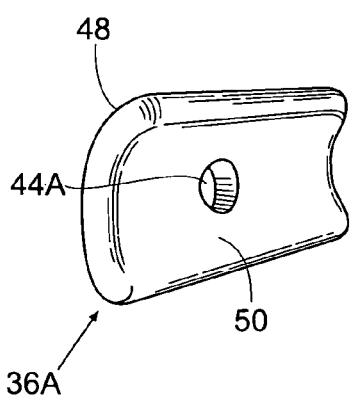
FIG. 8 is a perspective view of a primary magnet shown in FIG. 7 and configured for attachment to the uvula.

As best seen in FIG. 8, the front side 48 and the back side 50 of the magnet 36A provide a concave, or sectorial, configuration, to approximate the contour of the anterior surface of the uvula. A screw stud hole 44A permits passage of the stud 42 to allow attachment of the magnet 36A to the uvula 32. The edges of the magnet 36A are desirably rounded or radiused, to prevent irritation of surrounding tissue. This provides increased comfort to the individual.

Figure 9:
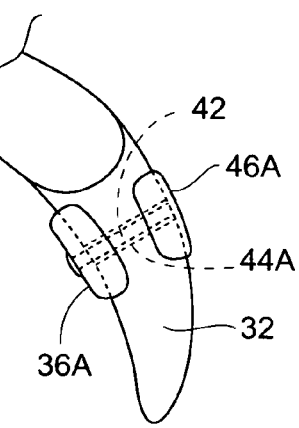
FIG. 9 is a side view illustrating attachment of a primary magnet on the uvula using a stud and backing plate.

As seen in FIG. 9, the magnet 36A is placed on the anterior surface of the uvula 32. A stud 42 is passed through the screw stud hole 44A and the magnet 36A is secured in place by the backing plate 46A.

Figure 10A:
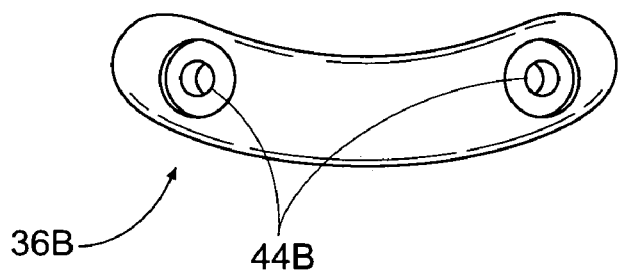
FIG. 10A is a front view of a primary magnet configured for attachment to the soft palate.
Figure 10B:
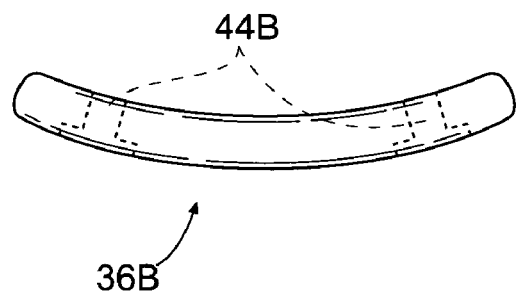
FIG. 10B is a side view of the magnet shown in FIG. 10A.

As FIGS. 10A and 10B show, the soft palate primary magnets 36B have a bowed configuration to approximate the contour of the arch of the soft palate 30, e.g., kidney bean shape. Similar to primary magnet 36A, rounded or radiused edges are provided to prevent irritation of surrounding tissue.

Figure 11:
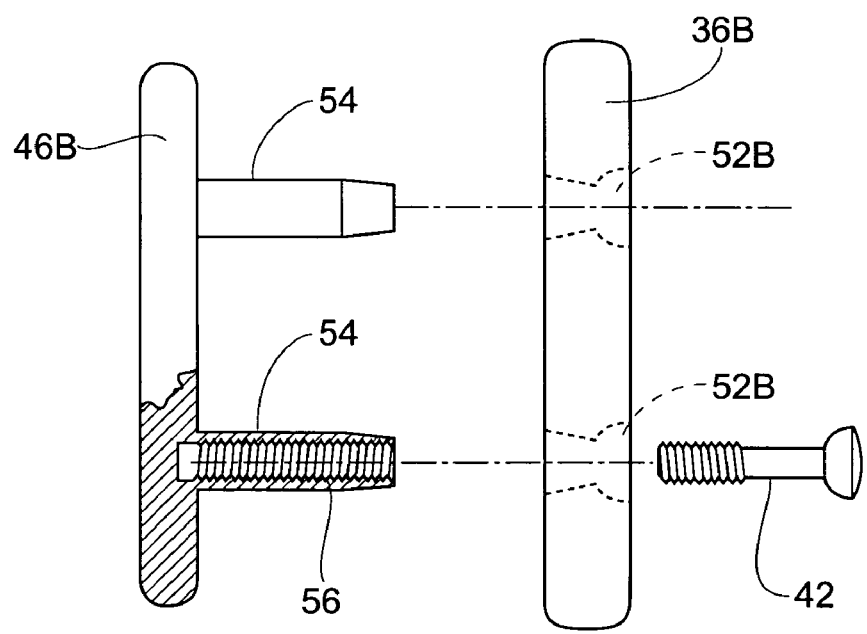
FIG. 11 is a side view and illustrating the use of a stud to secure a magnet of the type shown in FIGS. 10A and 10B to a complementary backing pad.

With reference to FIG. 11, a conformal backing plate 46B serves to secure attachment of the magnet 36B to the soft palate 30. In the arrangement shown in FIG. 11, the plate 46B includes a pair of pins 54 (left and right), each pin having a bore 56 to receive and secure a stud 42, e.g., by threaded engagement. The magnet 36B includes a pair of screw stud holes 52B (left and right) that register with the pins 54. The holes 52B are desirably tapered and configured to receive the pins 54 and permit passage of studs 42 to secure attachment of the magnet 36B.

B. Oral Appliances for Removably Mounting the Secondary Magnet in the Oral Cavity 1. First Embodiment Referring now to FIGS. 12A, 12B, and 13, the system includes an oral appliance 40 to carry the secondary magnet 38 within the oral cavity 20. Desirably, the oral appliance 40 is configured for convenient temporary placement into and removal from the oral cavity 20.

As before explained, the secondary magnet 38 is complementary to the primary magnet 36, i.e., the primary and secondary magnets 36 and 38 are of opposite polarity.

Figure 12A:
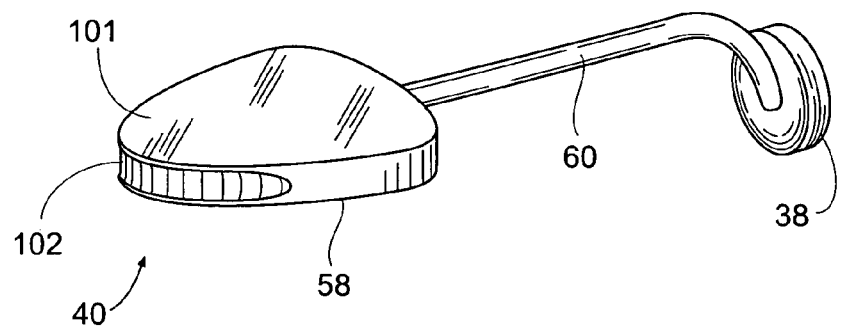
FIG. 12A is a top perspective view of a soft pad oral appliance device with flexible, movable mounting stem and secondary magnet at the distal end which embodies features of the invention.
Figure 12B:
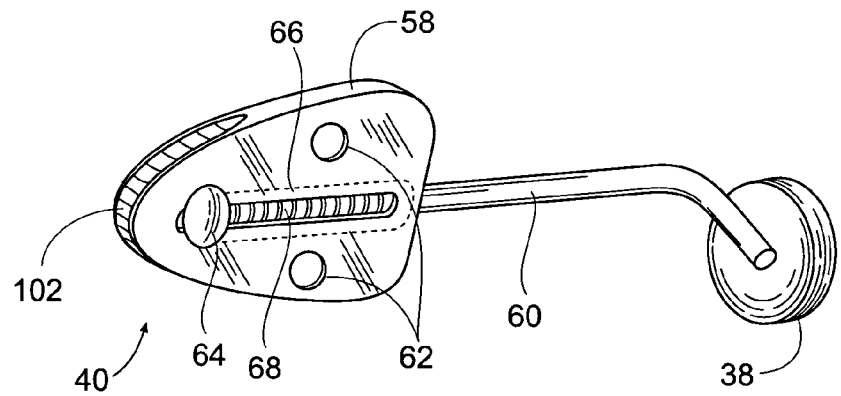
FIG. 12B is a bottom perspective view of the soft pad oral appliance device shown in FIG. 12A.

As shown in FIGS. 12A and 12B, the appliance 40 comprises a base pad 58 and a support stem 60. The support stem 60 carries one or more secondary magnets 38 on its far end. As seen in FIG. 12B, the bottom surface of the appliance 40 includes positioning holes 62, the function of which will be described later.

Figure 13:
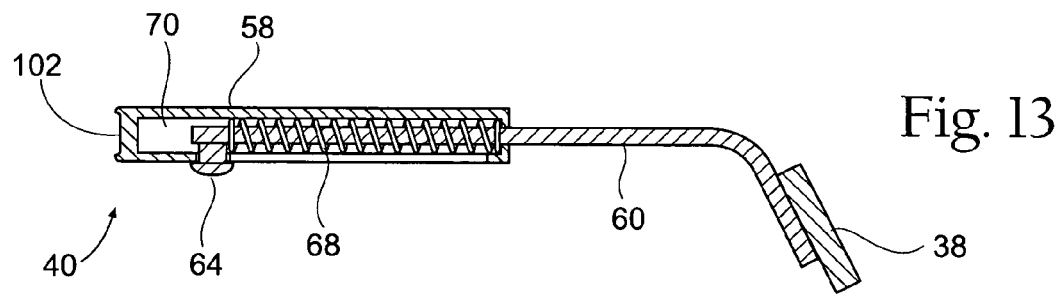
FIG. 13 is a side section view of the oral appliance shown in FIG. 12A.

The bottom surface also carries a slidable knob 64, which forms the near end of the support stem 60. As FIG. 13 shows, the knob 64 works against a spring 68 within the base pad 58. The spring 68 biases the support stem 60 and secondary magnet 38 toward an anterior position in the oral cavity 20. The spring 68 nevertheless accommodates transitory movement of the secondary magnet 38 toward a more posterior direction. More particularly, the spring 68 allows the secondary magnet 38 to follow transitory anterior-posterior movement of the more mobile primary magnet 36, e.g., during swallowing, while still urging the primary magnet 36, and, with it, the mobile tissue attached to it, toward a desired anterior position.

In use, as shown by an arrow in FIG. 3, the knob 64 can be manipulated by the wearer to slide the secondary magnet 38 toward the rear of the mouth 20, and thus toward the primary magnet(s) 36 affixed to the soft palate 30. As attraction between the magnets 36 and 38 occurs, the wearer can release the knob 64. When released, the spring 68 urges the stem 60 (and secondary magnet 38) toward an anterior position within the mouth 20. The tissue of the soft palate 30 and uvula 32 are thereby urged forward toward a desired anterior position, as depicted by phantom lines in FIG. 3, to prevent the tissue of the soft palate 30 from falling back into the airway.

The spring 68 is designed to place a light pulling force in the range of 2 to 50 grams on the primary magnet(s) 36 affixed to the soft palate 30. It is believed that these low pulling forces are sufficient. The light pulling forces further provide comfort to the wearer and avoid irritation to the tissue.

The base 58 of the appliance 40 can be constructed of a resilient, soft elastomeric material such as silicon rubber, or may alternatively be made of a closed-cell polymeric foam. These soft materials allow the body of the device to conform to the roof of the mouth 20, which can varies greatly among individuals. The base 58 can be positioned within the oral cavity 20 and attached to the roof of the mouth 20 using a high-tack adhesive compatible with the oral cavity 20, such as that used to secure dentures to gums.

Desirably, the interior surface of the bore 70 (see FIG. 13), in which the stem 60 and the spring 68 are positioned, is injection molded of a rigid, thermoplastic material such as ABS, acetal, or polypropylene to provide smooth sliding action for the stem 60. The appliance 40 may be overmolded by the soft material of the base pad 58, or the appliance 40 may be inserted and bonded into a recess in the base pad 58. This hybrid structure for the appliance 40 provides dimensional integrity needed to prevent binding of the moving parts, which might result from having the bore 70 located directly in the compliant material, while nevertheless allowing the base 58 to be soft and conformable enough to fit a wide variation in shape and contour of the roof of the mouth 20.

In use, the opposing pole magnets 36 and 38 may make physical contact with each other. Alternatively, the opposing pole magnets 36 and 38 may be positioned so that they are magnetically attracted to one another without physical contact.

There may be one or more primary magnets 36 attached to the uvula 32 and/or soft palate 30, as previously described and as shown in FIGS. 4 and 5.

The appliance 40 is desirably configured for easy insertion into and removal from the oral cavity 20 by the wearer. Thus, the appliance 40 may be used only during sleep and removed upon awakening. Removal of the appliance 40 during waking hours prevents any interference with swallowing, speech, or other routine activities.

A physician can initially fit the appliance 40 to an individual's mouth 20. The physician visually determines the appropriate position within the mouth 20 to properly pull the soft palate 30 and uvula 32 in an anterior direction and to the desired degree. To aid the individual to subsequently position the appliance 40 within the mouth 20, a positioning tool 72 is desirably supplied with the appliance 40.

Figure 15:
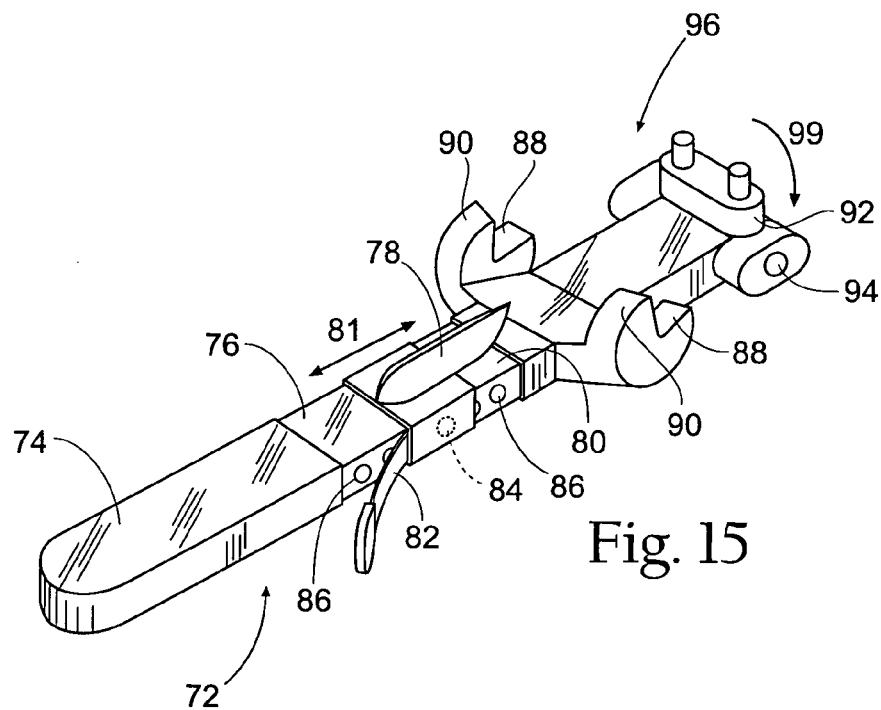
FIG. 15 is a perspective view of the positioning tool shown in FIG. 14.

FIGS. 14 and 15 show a representative embodiment for a positioning tool 72 suitable for this purpose. The tool 72 desirably includes a handle 74. The handle 74 can be molded integrally with a carrier back 76, which extends for the entire length of the tool 72.

A center pointer 78 is molded as a part of a slider 80. The fore and aft position of the slider 80 is desirably fixed by the physician when customizing the tool 72 to the individual, as represented by arrow 81 in FIG. 15. A locking tab 82 holds an interior locking pin 84. When the physician sets the slider 80 in the desired location, the locking tab 82 can be withdrawn, allowing the internal locking pin 84 to engage openings 86 in the carrier back 76. The slider 80 is thereby permanently set by the physician in the desired position customized for the individual.

Notches 88 and upright fingers 90 form a receiver for the lateral incisors, to provide a positioning feature that allows the tool 72 to accurately place the base 58 of the appliance 40 in the roof of the mouth 20. A rotatable member 92 pivots about a pivot pin 94 and is subject to a light friction to prevent undesirable rotation.

The tool 72 further includes a pair of positioning pins 96, which extend from the rotatable member 92. The pins 96 register with and enter the positioning holes 62 on the appliance 40, as previously described. The patient places the base 58 on the tool 72 by pressing the base 58 onto the pins 96 to engage the positioning holes 62 with the pins 96. The elastic nature of the compliant material in the base 58, along with a hole diameter slightly smaller than the diameter of the standing pins 96, causes the base 58 of the appliance 40 to be frictionally held on the rotatable member 92.

Once the appliance 40 is fitted to the positioning tool 72, the patient applies a prescribed amount of adhesive (not shown) to the top surface of the base 58. Manipulating the positioning tool 72 like a tongue depressor, the individual positions the tool 72 in the oral cavity 20 (see FIG. 14).

While standing in front of mirror, the individual aligns the pointer 78 with the interdental space between the two upper incisors. The individual also brings the notches 88 into contact with the occlusal surface of the lateral incisors, with the upright fingers 90 pressing against the anterior surface of the upper teeth(because the physician has previously adjusted the center pointer 78 to the appropriate fore and aft position, as previously described, it is not necessary for the individual to make any further adjustments).

With the handle 74 held horizontally (depicted in solid lines in FIG. 14), the individual holds the positioning tool 72 against the upper teeth. The individual pivots the exposed handle end 74 of the tool 72 downward (as depicted by the arrow and phantom lines in FIG. 14). The far end 98 of the appliance 40 swings in an upward arc toward the roof of the mouth 20, as represented by phantom lines in FIG. 14. As the appliance 40 moves upward, the stem 60 of the appliance 40 makes contact with the hard palate 28 at a desired point 100. This causes the rotatable member 92 to swing (depicted by arrow 99 in FIG. 15) bringing the top surface of the base 58 (with the dental adhesive material) into an orientation that is parallel to the roof of the mouth 20, and in a position selected by the physician when the appliance 40 was originally fitted.

After holding a light pressure upward for a short time period, e.g., approximately 10 seconds, the individual pulls the positioning tool 72 downward to release it from the base 58, leaving the appliance 40 affixed to the roof of the mouth 20 in the desired position. Upon removing the tool 72, the individual can use a thumb or finger to press the base 58 into intimate contact with roof of the mouth 20 and set the bond.

Referring again to FIG. 3, the patient then places a finger on the knob 64 to move the knob 64 as depicted by an arrow in FIG. 3 toward the back of the mouth 20 to bring the primary magnet(s) 36 into attraction with the secondary magnet(s) 38, thereby pulling the soft palate 30 and uvula 32 into a forward, stabilized position.

To remove the appliance 40, the patient uses a fingertip to peel the flexible base 58 away from the roof of the mouth 20. In one embodiment (see FIGS. 12A and 12B), the anterior end 101 of the appliance 40 can include a groove or chamfer 102 to facilitate peeling the base pad 58 away from the roof of the mouth 20, as also shown in FIG. 14. The remaining adhesive can be removed by brushing with a toothbrush. To reuse the appliance 40, the patient peals off the remaining adhesive attached to the base 58 by using a fingertip to roll the adhesive off of the top surface of the base 58.

The appliance 40 may, alternatively, be of a modular design, allowing the soft compliant base 58 to be a disposable component into which the tool 72 may be placed and withdrawn for re-use the next night. The disposable base 58 may contain a pressure sensitive adhesive to eliminate the need to use and apply a liquid adhesive.

2. Second Embodiment

Figure 16:
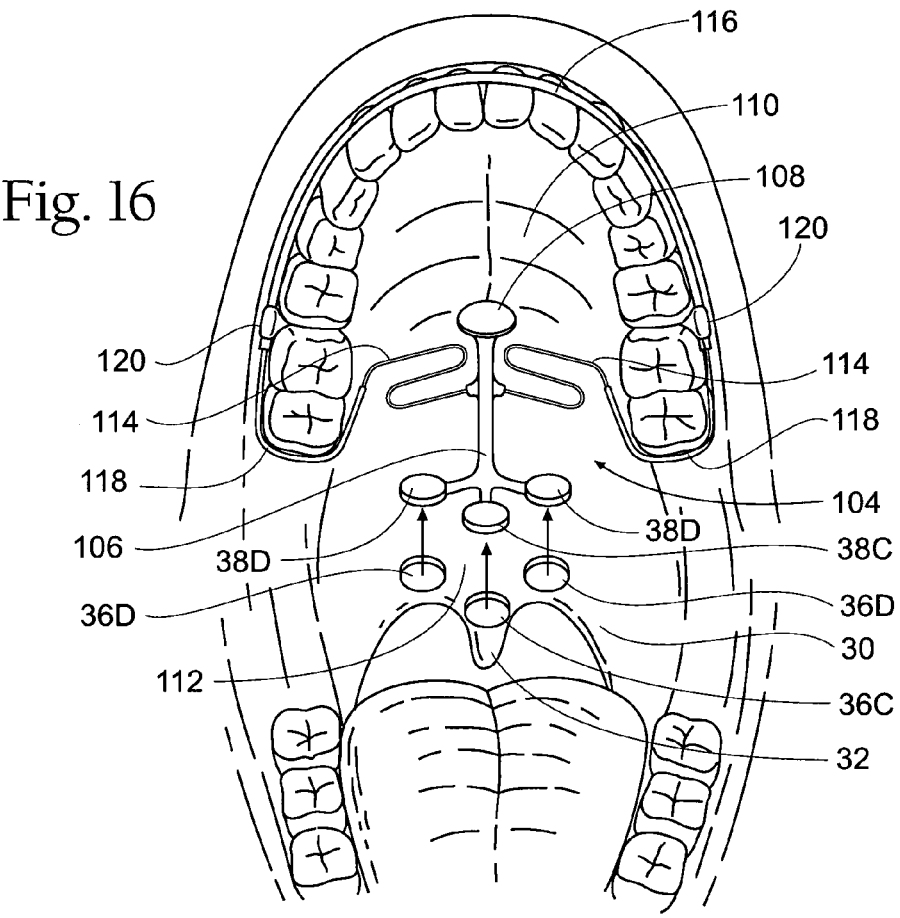
FIG. 16 is an anatomical view of a human oral cavity illustrating the placement of an alternative embodiment of an oral appliance embodying features of the invention within the oral cavity.
Figure 17:
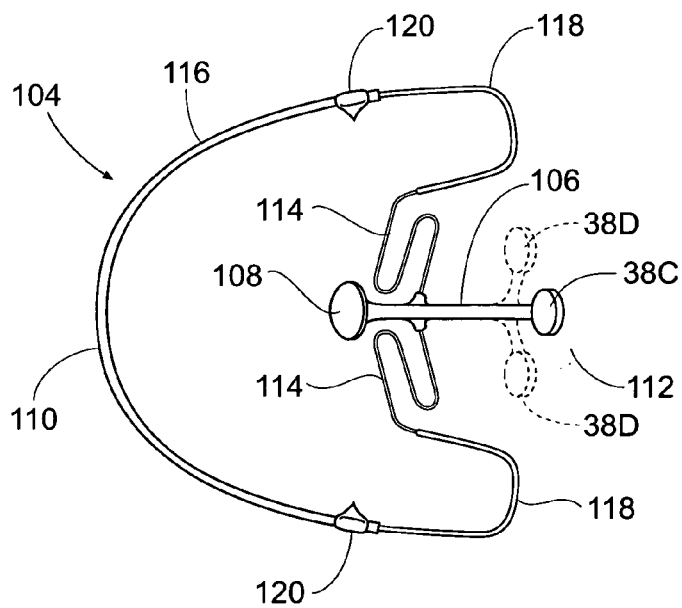
FIG. 17 is a bottom view of the oral appliance shown in FIG. 16.
Figure 18:
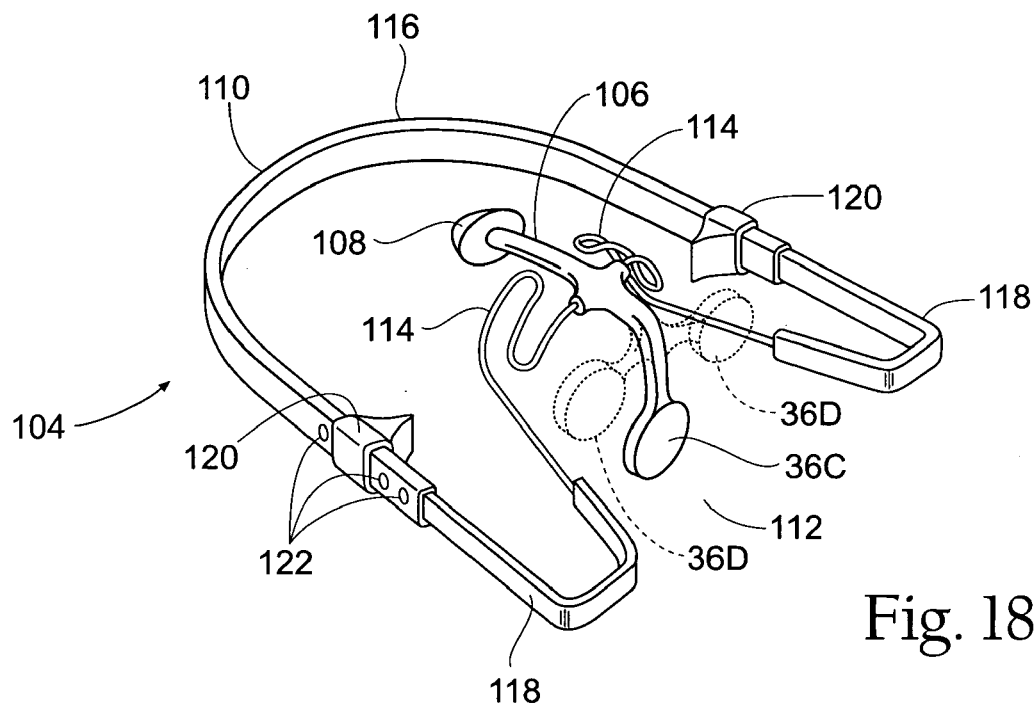
FIG. 18 is a perspective view of the oral appliance shown in FIG. 16.

FIGS. 16 to 18 show another representative embodiment of an appliance 104 that can be releasably mounted in the oral cavity 20, to hold one or more secondary magnets 38 in alignment with one or more primary magnets carried by the soft palate and/or uvula.

In this arrangement, secondary magnets 38C and 38D are mounted on a stem portion 106 having a knob 108 at the anterior end 110 of the appliance 104. The secondary magnet 38C is positioned at the posterior end 112 of the stem 106 and is complementary to primary magnet 36C attached to the uvula 32 (see FIG. 16). Desirably, a pair of secondary magnets 38D also extend radially from the stem 106, just posterior to the secondary magnet 38C. The secondary magnets 38D align with and complement the primary magnets 36D attached to the soft palate 30.

Spring wires 114 extend radially from the stem 106. In this embodiment, the appliance 104 is held in place by use of an elastic band 116. In use, the band 116 is stretched around the outer faces of the upper teeth. The appliance 104 can also be anchored at the posterior surface of the molars by a pair of hooks 118 which couple with the spring wires 114.

Indexing locators 120 can be provided to permit the position of the hooks 118 to be adjustable posteriorly and anteriorly for proper fit. The indexing locators 120 may be adjusted by the physician to fit into the interdental spaces between the molars and then locked in place to provide a repeatable positioning of the appliance 104. As best seen in FIG. 18, a series of holes 122 are desirably provided for easy adjustment of the locators 120.

When in place, the appliance 104 is positioned to permit an attraction between the opposing magnetic poles and pull the tissue of the soft palate 30 and uvula 32 in an anterior direction, as depicted by arrows in FIG. 16.

Figure 19:
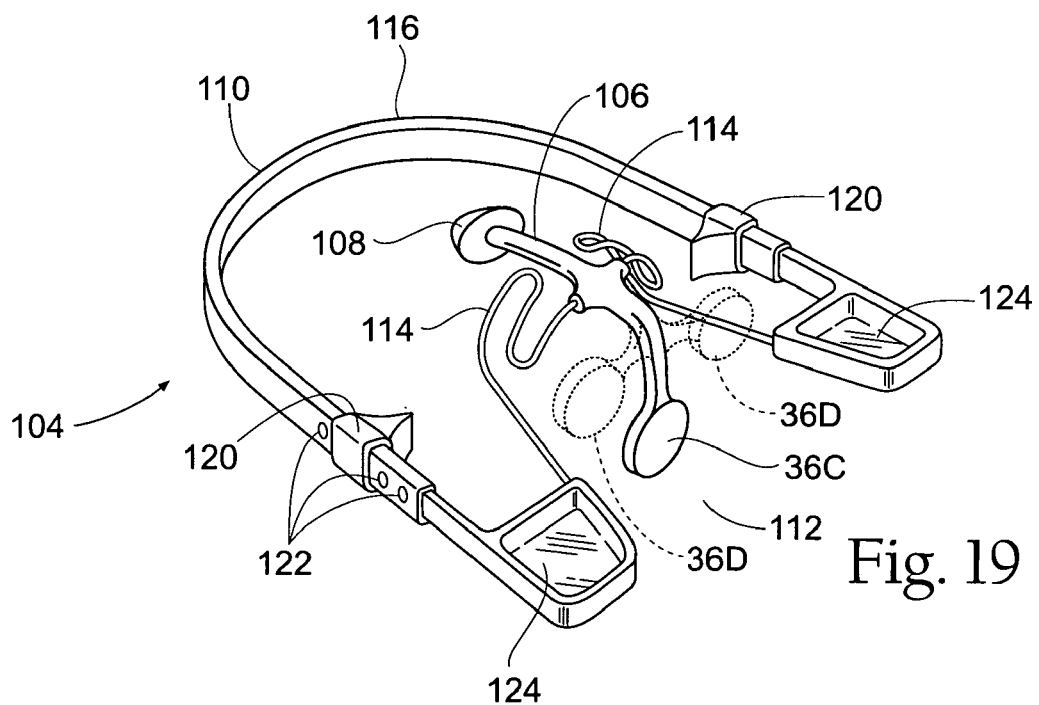
FIG. 19 is a perspective view of an alternative embodiment of the oral appliance shown in FIG. 18.

As shown in FIG. 19, the hooks 118 may be replaced by molded trays 124 into which the patient may place a small amount of dental adhesive (not shown). In this embodiment, the band 116 is desirably a non elastic material such as a nylon with a soft covering, preferably a silicone rubber. The patient slips the band 116 of the appliance 104 over the front surface of the upper teeth and with the dental adhesive already in the molded trays 124, presses the trays 124 upward into intimate contact with the upper rear molars.

It should be appreciated that the oral appliance for holding one or more secondary magnets in alignment with one or more primary magnets, carried by the soft palate and/or uvula, can be custom formed to the individual's hard palate. This arrangement would make possible an established and familiar way of placing a dental/oral appliance in the mouth.

3. Third Embodiment

Figure 24:
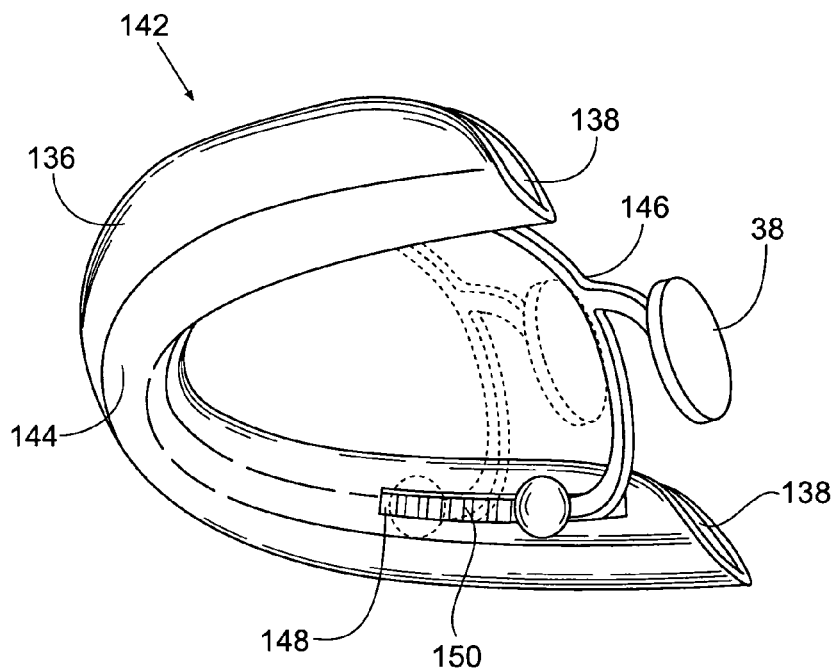
FIG. 24 is a perspective view of an oral appliance embodying features of the invention.
Figure 25:
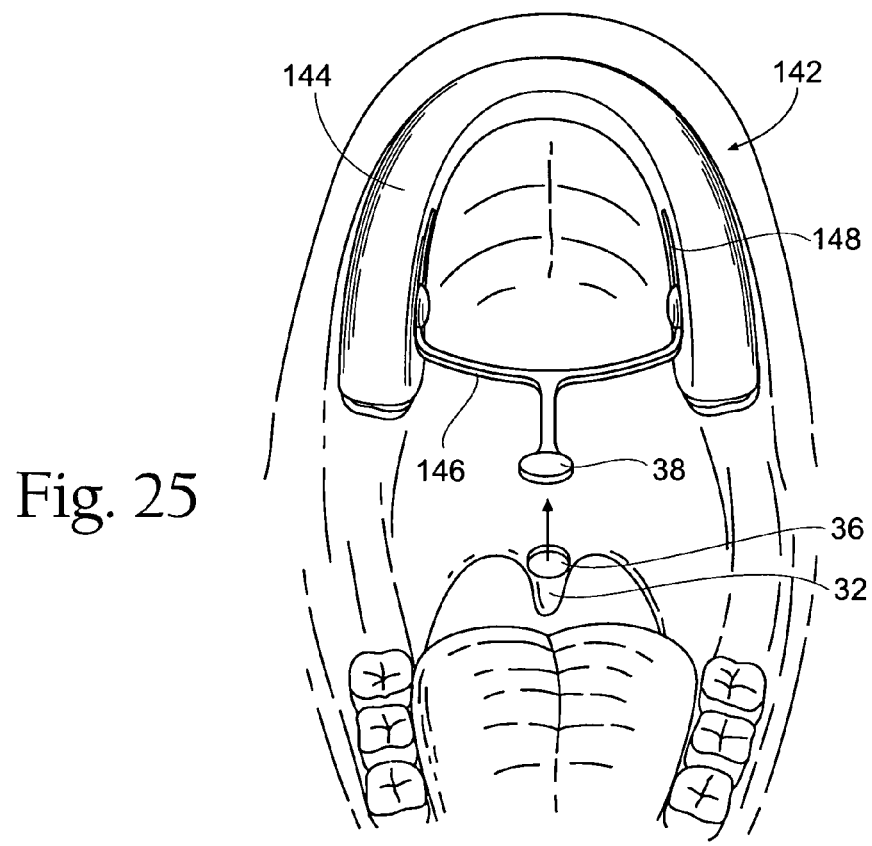
FIG. 25 is an anatomical front view of a human oral cavity illustrating the placement of the appliance of FIG. 24 over the upper teeth.

FIGS. 24 and 25 show another alternative embodiment of an oral appliance 142 that can be releasably mounted in the oral cavity 20, to hold one or more secondary magnets 38 in alignment with one or more primary magnets carried by the soft palate and/or uvula.

In this embodiment, the appliance 142 comprises a generally U-shaped body 144. One or more secondary magnets 38 are carried by a bar 146 extending from slots 148 on the medial surface of the body 144.

The body 144 is a generally hollow body having an open top 136 and open ends 138, sized and configured to rest on the upper teeth, as seen in FIG. 25. Placement of the appliance 142 on the upper teeth results in attractive magnetic forces (represented by an arrow in FIG. 25) between the primary and secondary magnets 36 and 38, drawing the primary magnet 36 toward the secondary magnet 38, thereby pulling the uvula 32 and soft palate 30 into a forward, stabilized position.

The bar 146 can be configured for adjustment by anterior or posterior movement, as represented by phantom lines in FIG. 24. This adjustment permits the secondary magnet 38 to be positioned properly in relation to the primary magnet 36 to effect the desired movement of tissue. In the illustrated embodiment, the slots 148 have a ratcheted surface 150 on which the bar 146 may be moved in fore and aft directions. Of course, other mechanisms may be used to provide such movement.

III. Another System Overview (Primary Magnet Configured for Anterior Movement of the Tongue)

As previously discussed, the tongue 34 is frequently the primary cause of apneic events. During sleep, tongue muscles can relax and allow the tongue 34 to move in a posterior direction and contact the pharyngeal wall, occluding the oropharynx 18 (see FIG. 1). If the tongue 34 is in the position described at the point of completing the exhalation cycle, it can act as a check valve, preventing inhalation.

FIGS. 20 to 23 illustrate one embodiment of another system for treating sleep-related breathing disorders such as snoring, upper airway resistance syndrome and obstructive sleep apnea. The system includes at least one primary magnet 36' implanted or otherwise affixed to the tongue 34, which can be used in association with a complementary secondary magnet 38' to position, stabilize and maintain the tongue in a preferred orientation in the oral cavity and airway, in both humans and animals. By moving and stabilizing the tongue in a desired location, the system mediates or prevents the obstruction of the upper airway that results in sleep-related breathing disorders.

In the embodiment illustrated in FIGS. 20 to 23, the primary magnet 36' is of opposite polarity from the secondary magnet 38', e.g., the North pole of the primary magnet 36 is oriented to face the South pole of the secondary magnet 38, or vice versa. The primary and secondary magnets 36' and 38' are therefore complementary, i.e., they are mutually oriented so that the force of magnetic attraction draws the primary magnet 36' toward the secondary magnet 38'.

As previously described, the secondary magnet 38' is intended to be carried in or by relatively immobile tissue, or at least mounted more securely than the primary magnet 36'. The primary magnet 36 is intended to be carried in or by more mobile tissue. Thus, as the more mobile primary magnet 36' is drawn toward the less mobile secondary magnet 38', a desired movement of tissue occurs.

It should again be appreciated that either magnet 36' or 38' may exert a magnetic force on a material that is not magnetized. Therefore, one of the magnets 36' or 38' can be replaced by a material, e.g., ferrous plate, on which the remaining magnet 36' or 38' is able to exert an attractive magnetic force. Of course, a ferrous plate could not exert a repelling force without being magnetized.

In FIGS. 20 to 23, the primary magnet 36' is carried by the more mobile tissue of the tongue 34. The secondary magnet 38' is carried by an oral appliance 126, which is releasably mounted to less mobile tissue (i.e., the lower teeth) along the floor of the mouth. Technical features of the holder 126 will be described in greater detail later.

Arranged in a complementary manner, the less mobile secondary magnet 38' acts upon the more mobile primary magnet 36' to draw the primary magnet 36, and, with it, the tongue 34, in an anterior direction (depicted by arrows in FIG. 23) to prevent obstruction of the airway.

A. Primary Magnet(s)

Figure 20:
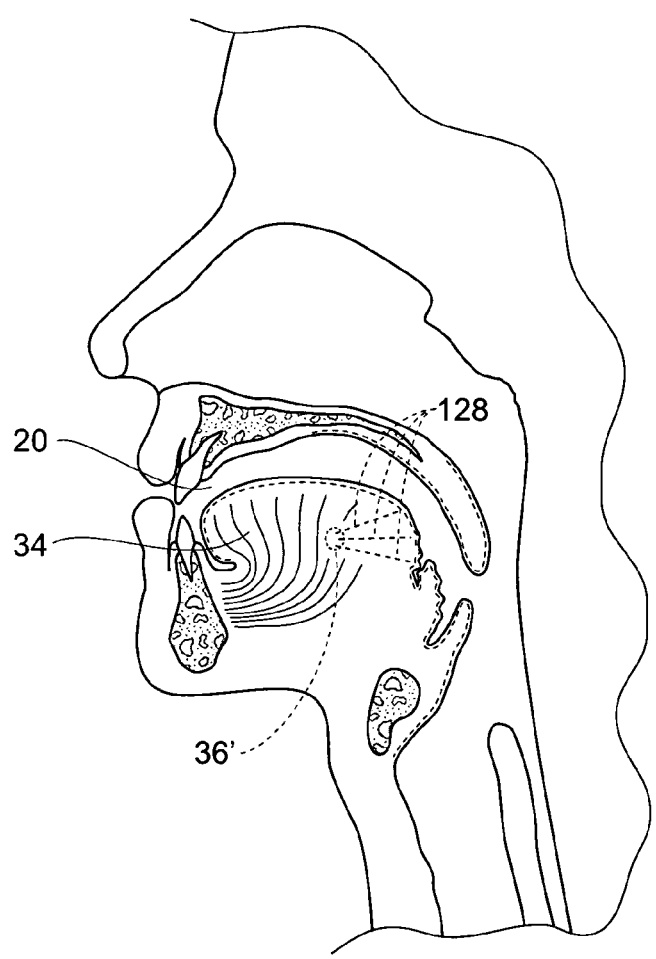
FIG. 20 is an anatomical cross-section of a normal human nasal airway, oral cavity, and oropharynx showing the placement of a primary magnet within the tongue to effect anterior movement of the tongue.
Figure 21:
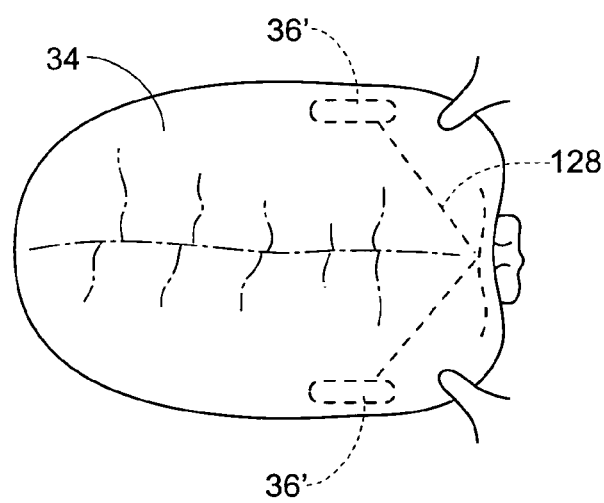
FIG. 21 is a top view of the tongue shown in FIG. 20 and illustrating the placement of primary magnets in the opposing lateral margins of the tongue to effect anterior movement of the tongue.

FIGS. 20 and 21 show a representative embodiment in which two primary magnets 36' are implanted in the opposing lateral margins of the tongue 34. The secondary magnet 38' is carried by an oral appliance 126 and interacts with the primary magnet 36' to effect anterior movement of the tongue 34 (see, e.g., FIG. 22). Sutures, bands or strips 128 can be implanted into the posterior of the tongue 34 and fastened to the magnets 36' to help pull the tongue 34 forward and distribute the forces of magnetic attraction more evenly within the tongue 34.

The magnets 36' can be coated with a fibrous or textured polymer layer to promote in growth of tissue into the coating. Tissue in growth will help to anchor the magnets 36' and reduce the possibility of migration of the magnets 36' caused by pulling forces.

Figure 22:
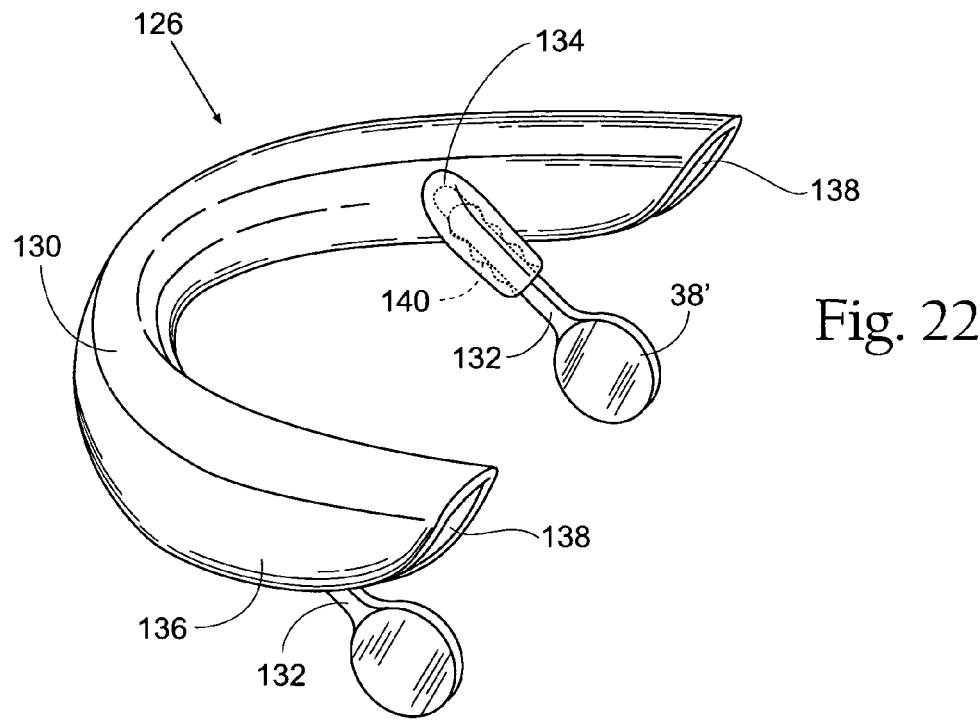
FIG. 22 is a perspective view of an oral appliance embodying features of the invention.
Figure 23:
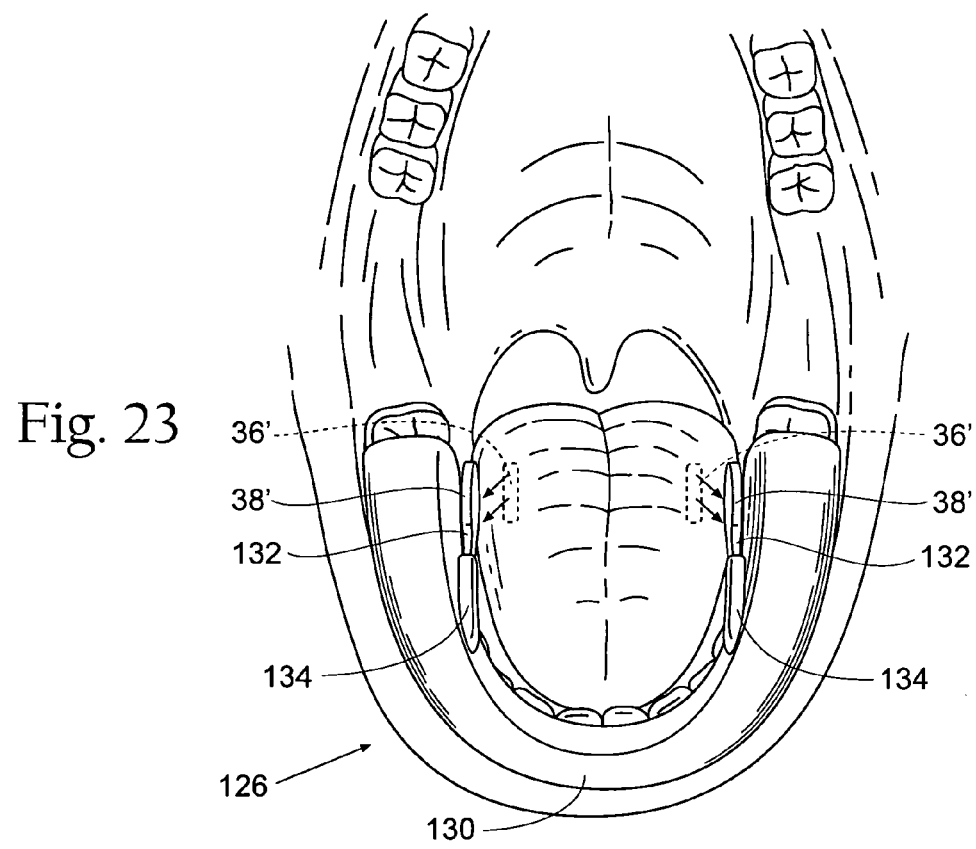
FIG. 23 is an anatomical front view of a human oral cavity illustrating the placement of the appliance of FIG. 22 over the bottom teeth.

B. Oral Appliances for Removably Mounting Secondary Magnet(s) within the Oral Cavity FIGS. 22 and 23 illustrate one embodiment of an oral appliance 126 that can be releasably mounted in the oral cavity 20, to hold one or more secondary magnets 38' in alignment with one or more primary magnets 36' implanted within the tongue 34, to affect anterior movement of the tongue 34. The oral appliance 126 can be variously configured to permit conduction of magnet forces between the primary and secondary magnets 36' and 38'.

Like the appliance 40, the appliance 126 is desirably configured for easy insertion and removal, so that it may be used only during sleep and removed upon awakening. Removal of the appliance 40 during waking hours prevents any interference with swallowing, speech, or other routine activities.

The appliance 126 comprises a generally U-shaped body 130 and a pair of secondary magnets 38' (right and left) carried by arms 132 extending from connectors 134 on the medial surface of the body 130.

The body 130 is a generally hollow body having an open bottom 136 and open ends 138, sized and configured to rest on the bottom teeth, as seen in FIG. 23. Placement of the appliance 126 on the bottom teeth aligns with secondary magnets 36' with the primary magnets 34'. This results in attractive magnetic forces (represented by arrows in FIG. 23) between the primary and secondary magnets 36' and 38'. The complementary magnets 36' draw primary magnets 36' toward secondary magnet 38', thereby pulling the tongue 34 into a forward, stabilized position.

The arms 132 can be configured for adjustment by anterior or posterior movement. This adjustment permits the secondary magnets 38' to be positioned properly in relation to the primary magnets 36' to effect the desired movement of tissue. In the illustrated embodiment, the connector 134 has a ratcheted surface 140 on which the arm 132 may be moved in anterior and posterior directions. Of course, other mechanisms can be used to provide this adjustment.

Figure 26:
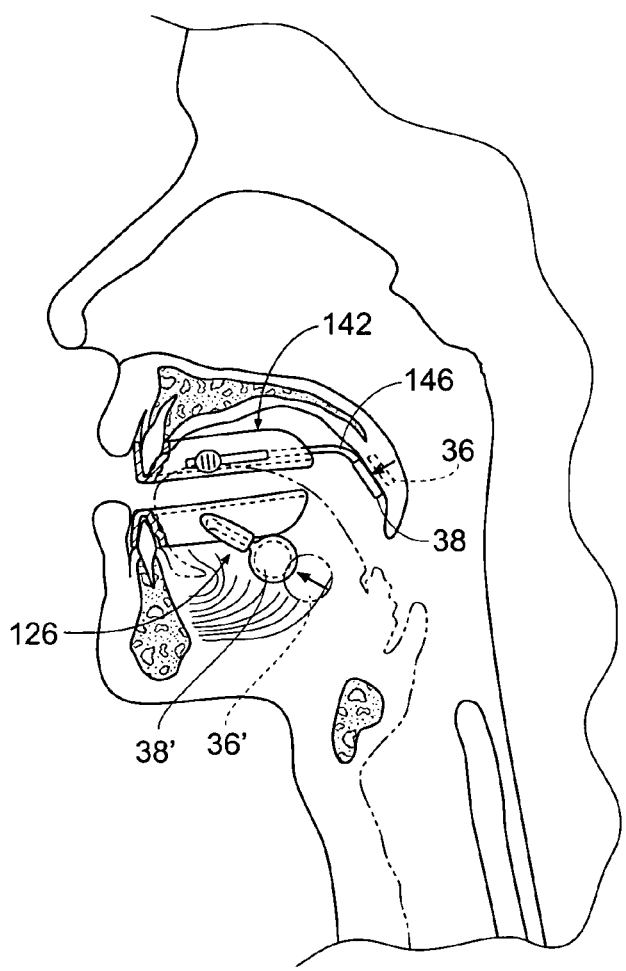
FIG. 26 is an anatomical cross-section of a human nasal airway showing the placement of the appliances of FIGS. 22 and 24 within the oral cavity.

FIG. 26 illustrates the use of the upper appliance 142 previously discussed and shown in FIGS. 24 and 25) in combination with the lower appliance 126. As FIG. 26 shows, the upper appliance 142 acts to effect anterior movement (depicted by an arrow) of the soft palate 30 and uvula 32. The lower appliance 126 acts to effect anterior movement (depicted by an arrow) of the tongue 34. In this arrangement, the appliances 126 and 142 cooperate to maintain a desired position of the soft palate 30, uvula 32, and tongue 34 to mediate or prevent obstruction of the upper airway that results in sleep-related breathing disorders.

Figure 27:
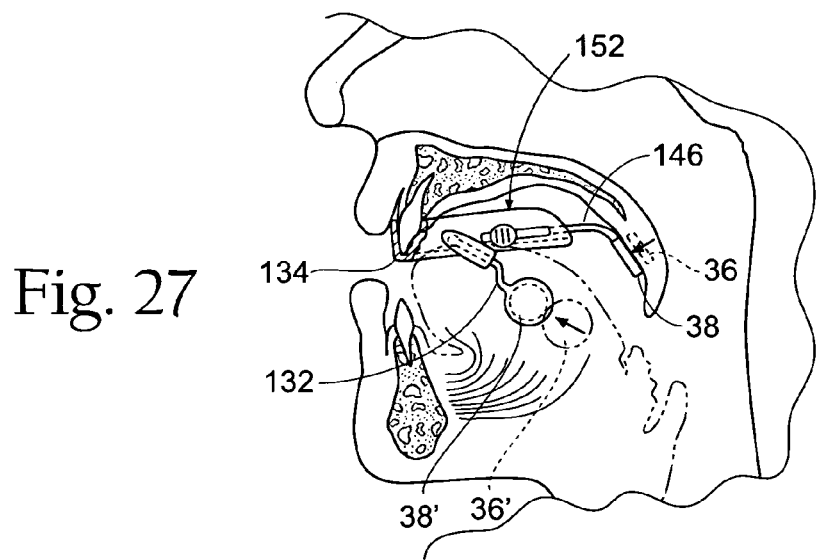
FIG. 27 is an anatomical cross-section of a human nasal airway showing an alternative embodiment of the oral appliance shown in FIG. 24.

In another alternative embodiment, shown in FIG. 27, a single appliance 152 carries both secondary magnets 38 and 38'. The appliance 152 is configured for placement over the upper teeth and is similar to the embodiment of the appliance 142 shown in FIGS. 24 and 25. However, a pair of secondary magnets 38' (right and left) are carried by arms 132 extending from connectors 134 on the medial surface of a U-shaped body 152 similar to the embodiment shown in FIGS. 23 and 24. Thus, in this arrangement, a single appliance serves to effect movement of the soft palate 30, uvula 32, and tongue 34 to mediate obstruction of the upper airway that results in sleep-related breathing disorders.

IV. Another System Overview (Primary Magnet Attached to Epiglottis with External Secondary Magnet)

Figure 28:
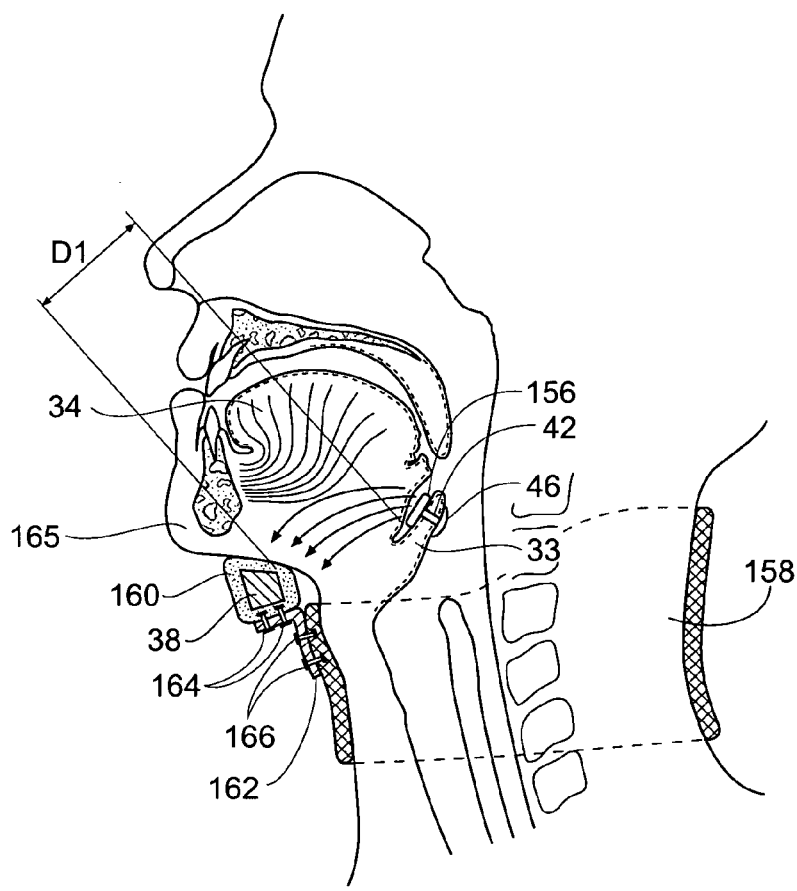
FIG. 28 is an anatomical cross-section of a human upper airway illustrating an alternative embodiment of the invention in which a primary magnet is attached to the epiglottis and a secondary magnet is carried by an external neck collar.
Figure 29:
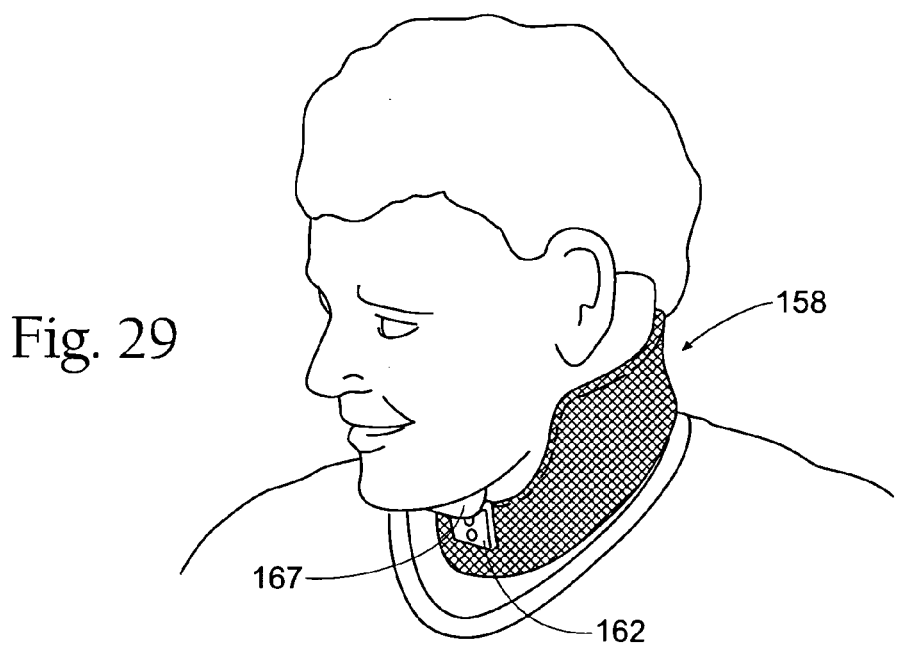
FIG. 29 is a perspective view of an alternative embodiment of the collar shown in FIG. 28.

FIGS. 28 and 29 illustrate one embodiment of another system for treating sleep-related breathing disorders such as snoring, upper airway resistance syndrome and obstructive sleep apnea. The system includes at least one primary magnet 156 affixed to the epiglottis 33, which is used in association with a complementary secondary magnet 38 to position, stabilize and maintain the tongue in a preferred orientation in the oral cavity and airway in both humans and animals. The complementary magnetic forces serve to support and move the tongue 34 forward to prevent contact between the back of the tongue 34 and the pharyngeal wall, thus preventing occlusion of the airway.

As previously described, the secondary magnet 38' is intended to be carried in or by relatively immobile tissue, or at least mounted more securely than the primary magnet 36'. In the illustrated embodiment, the secondary magnet 36 is carried by a collar 158 worn externally about the neck. The primary magnet 156 is intended to be carried in or by mobile tissue. In the illustrated embodiment, the primary magnet 156 is affixed to the epiglottis. Thus, as the more mobile primary magnet 156 is drawn toward the less mobile secondary magnet 38, a desired movement of tissue occurs.

A. Primary Magnet(s)

In the illustrated embodiment, the primary magnet 156 comprises a ferrous plate 156 that is attached to the anterior surface of the epiglottis 33 and secured by a stud 42 and a flexible backing 46. As previously described, the ferrous plate 156 may alternatively be a magnet of metallic or rare earth composition. Thus, the plate 156 functions similar to primary magnet 36 previously described.

Multiple studs 42 may be used to affix the plate 156 (or magnet 36) to the epiglottis 33. Alternatively, the ferrous plate 156 (or magnet 36) may be implanted within tissue of the epiglottis 33.

The backing 46 is desirably thin, e.g., approximately 1 mm, and tapered at the edges to avoid catching food particles or causing discomfort to the patient. The means of securing the plate 156, stud 42, and backing 46 is preferably a releasable connection, such as a threaded screw and tapped hole or other secure means that can be removed by the physician.

B. Secondary Magnet(s)

A collar 158, carrying a secondary, focused energy magnet 38 similar in function to secondary magnets 38 previously described, is provided for wear during sleep. The collar 158 is desirably made of a webbing or other flexible belt-like material that is comfortable to the individual wearing it. For added patient comfort and convenience, the collar 158 is preferably covered in a soft cloth sleeve that may be slipped off of the collar and washed. Alternatively, a disposable cover (not shown) or an entirely disposable collar 158 may be employed.

The collar 158 may, in one embodiment, have an expandable (elastic) section, or it may be made entirely of an elastic belt material, so that the collar 158 may be comfortable and still provide stability for the magnet 38 mounted at the center front of the collar 158. The collar 158 is equipped with a means for adjusting to a wide range of neck sizes. Such adjustment may be by belt, buttons or snaps, but in the preferred embodiment would use a hook and loop fastener such as Velcro® to provide adjustability.

The focused energy magnet 38 is positioned within a soft casing 160, preferably of a polymer foam, and further attached to a mounting bracket 162, e.g., by adhesive or fastener 164. The mounting bracket 162 is secured to the adjustable collar 158, e.g., by adhesive or fastener 166, and positioned below the chin 165. The magnet 38 is of a high energy type, such as neodymium, and is sized and shaped to concentrate the magnetic flux in one direction. The magnet 38 may be encased in a shielding material to further focus and direct the magnetic force toward the ferrous plate 156.

The collar 158 maintains the magnet 38 at a distance D1 from the plate 156 and in position, to permit an attraction between the plate 156 and the magnet 38. The magnet 38 is oriented with the primary direction of magnetic flux being in a posterior-anterior direction, as depicted by arrows in FIG. 28. Due to the collar mounting bracket 162, the magnet 38 is held more securely in place than the plate 156. Therefore, attractive magnetic forces draw the plate 156 toward the magnet 38. In this arrangement, as the plate 156 is drawn forward toward the magnet 38, it places pressure on base of the tongue 34, thereby moving the tongue 34 in an anterior direction.

In an alternative embodiment, the magnet 38 may be an electromagnet for exerting an adequate pull at the distance required to effect proper positioning of the tongue 34. Such an electromagnet may be powered by a D.C. power supply or by a battery pack.

As shown in FIG. 29, the collar 158 may extend upward and sweep back behind the jaw 167, to prevent rotation of the collar 158 during sleep.

V. Overviews of Other Systems

A. Hyoid Bone Attachment

Figure 30:
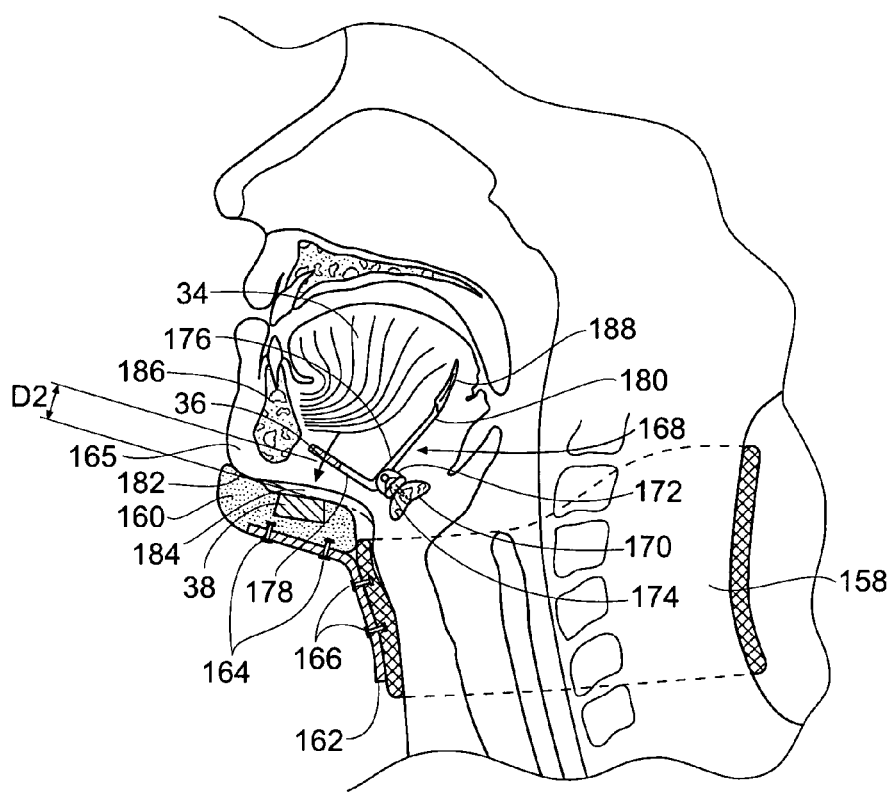
FIG. 30 is an anatomical cross-section of a human upper airway illustrating an alternative embodiment of the invention in which a primary magnet is carried by a fulcrum attached to the hyoid bone and a secondary magnet is carried by an external neck collar.

FIG. 30 shows another system for treating sleep-related breathing disorders such as snoring, upper airway resistance syndrome and obstructive sleep apnea. The system includes at least one primary magnet 36 implanted by surgical attachment to the hyoid bone 170, which is used in association with a complementary secondary magnet 38 externally worn on the chin, to position, stabilize and maintain the tongue in a preferred orientation in the oral cavity and airway in both humans and animals. The complementary magnetic forces serve to support and move the tongue 34 forward to prevent contact between the back of the tongue 34 and the pharyngeal wall, thus preventing occlusion of the airway.

The system shown in FIG. 30 includes a device 168 sized and configured to be implanted by surgical attachment to the hyoid bone 170 (the hyoid bone 170 is a horseshoe-shaped bone of anterior neck located at the base of the tongue 34).

The device 168 includes a fulcrum 172, which is affixed to the hyoid bone 170 by a bone screw 174. Extending from the fulcrum 172 is an actuator 176 having a generally horizontal first arm 178 and a generally vertical second arm 180.

Suitable material for arms 178 and 180 are an inert rigid material such as titanium, shaped memory alloy (Nitinol®), or a biologically compatible polymer such as reinforced polytetrafluoroethylene (Teflon®). Suitable materials, configuration, and length of arms 178 and 180 can be varied to maximize comfort and to minimize interference with swallowing and speech.

The primary magnet 36 is affixed to one end of the first arm 178.

A collar 158 carries the secondary magnet 38. The patient wears a collar 158 when asleep. The collar 158 is similar to the collar previously described and shown in FIGS. 28 and 29. However, as FIG. 30 shows, in this arrangement, the distance D2 between the primary magnet 36 and the secondary magnet 38 is considerably less than the distance D1 between the primary magnet 36 and the secondary magnet 38 shown in FIG. 28. As shown in FIG. 30, the collar 158 orientates the secondary magnet 38 such that the primary direction of magnetic flux (represented by an arrow in FIG. 30) attracts the primary magnet 36 in a downward direction.

The collar magnet 38 is encased in a soft casing material 160, preferably polymer foam, and affixed to a bracket 162, e.g., by adhesive or fastener 164, which is further affixed, e.g., by adhesive or fastener 166, to the collar 158 as was described for the earlier embodiment.

The material is configured to contact the chin 165 at 182, preventing the collar 158 from moving upward due to the magnetic pull or due to movement during sleep, assuring that comfort and proper position are maintained. A space 184 between the bottom of the chin 165 and the top of the secondary magnet 38 provides room for the tissue and muscle between the mandible 186 and the hyoid bone 170 to be pulled downwardly by the attraction between the secondary magnet 38 and the primary magnet 36.

As the primary magnet 36 is pulled downward, the tissue between the mandible 186 and hyoid bone 170 flexes downward, exerting a rotational force on the actuator arms 178 and 180, with the center of rotation being the fulcrum 172. At the upper end of the second arm 180 there is a paddle 188 configured to press in an anterior direction on the muscular tissue within the tongue 34. This action holds the tongue 34 in an anterior direction, preventing occlusion of the airway by the back of the tongue 34.

Figure 31:
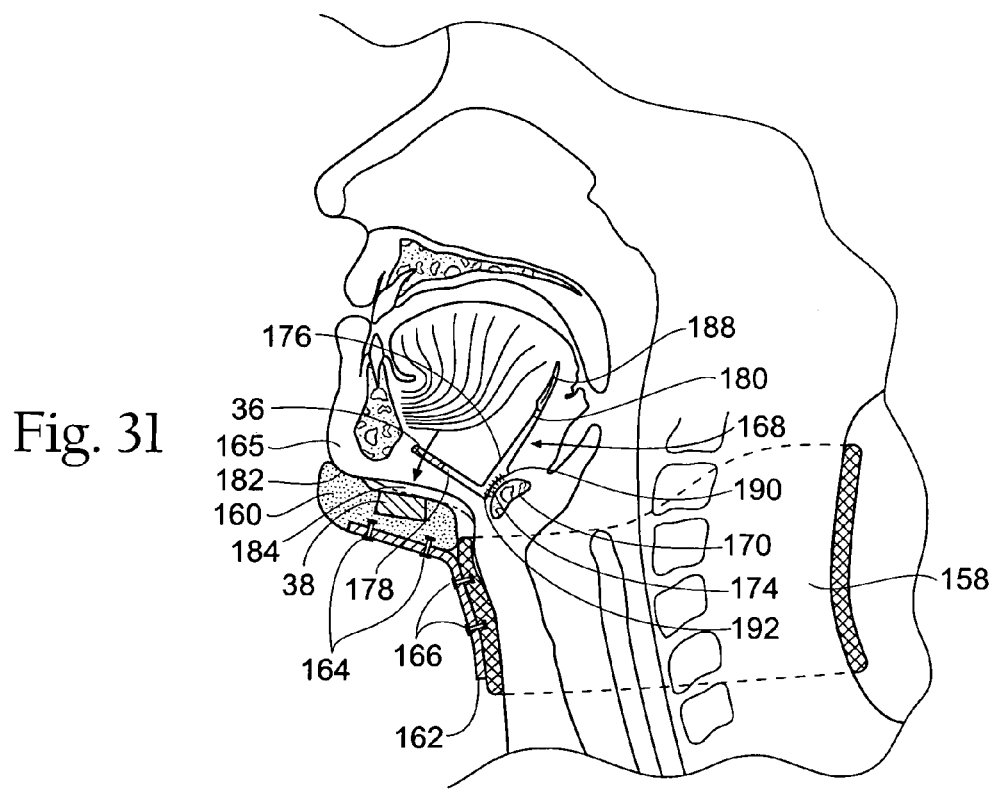
FIG. 31 is an anatomical cross-section of a human upper airway illustrating an alternative embodiment of the fulcrum shown in FIG. 30 and its placement in tissue in front of and above the hyoid bone.

In alternate embodiment (see FIG. 31), the actuator arms 178 and 180 extend from a U-shaped stirrup 190 providing a fulcrum point 192. The actuator 176 is positioned in front of and above the hyoid bone 170 and sutured in place to the soft tissue, leaving approximately 2 to 3 mm of tissue between the stirrup 190 and the hyoid bone 170. The actuator 176 is desirably coated with an expanded Teflon® PTFE (polytetrafluoroethylene) to encourage in growth of the tissue as the sutures 194 dissolve.

B. Mandible Attachment

1. First Embodiment

Figure 32:
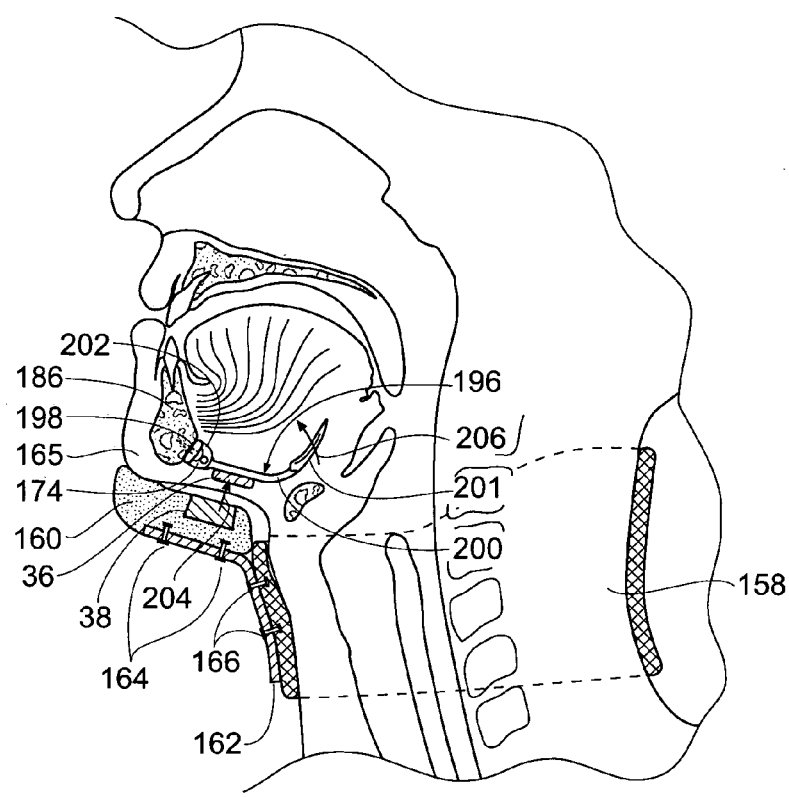
FIG. 32 is an anatomical cross-section of a human upper airway illustrating an alternative embodiment of the invention in which a primary magnet is carried by a device implanted into the mandible and a secondary magnet is carried by an external neck collar.

FIG. 32 shows another system for treating sleep-related breathing disorders such as snoring, upper airway resistance syndrome and obstructive sleep apnea. The system includes a device 196 carrying a more mobile primary magnet 36, which is implanted within the tongue 34, and a less mobile secondary magnet 38, which is carried by an external collar 158 against the chin.

The device 196 comprises a bracket 198 coupled to an arm 200. In this embodiment, the bracket 198 is affixed to the posterior portion of the mandible 186 using a bone screw 174 or other permanent means of attachment. The mandible 186 provides a stable platform.

The arm 200 is implanted into tongue tissue, reaching toward the back of the tongue 34 and sweeping upward. At the upper end of the arm 200 there is a paddle 201 configured to press in an anterior direction on the muscular tissue within the tongue 34.

The arm 200 is pivotally attached to the bracket 198 with the pivot or hinge 202 allowing rotational movement around a point near the upper rear edge of bracket 198. The primary magnet 36 is permanently affixed to the lower surface of the arm 200 approximately one-half of the way between the two ends of the arm 200.

A secondary magnet 38 is carried by an external collar 158, to be worn against the chin during sleep, as previously described. The secondary magnet 38 may be encased in a soft (preferably polymeric foam) pad 160 to provide comfort for the wearer, as previously described (see e.g., FIGS. 28 and 29). The foam pad 160 is affixed to and supported by a bracket 162 that is further affixed to a collar 158, as also previously described. However, in this arrangement, the mounting position of the magnets 36 and 38 are in a more posterior direction than that of the embodiment shown in FIGS. 30 and 31, to effectuate desired movement of the tongue 34.

In this arrangement, the polarities of the primary and secondary magnets 36 and 38 are non-complementary, i.e., the magnets 36 and 38 have like polarity. The like polarities establish repelling magnetic forces.

Thus, as depicted by arrow 204 in FIG. 32, due to the like polarities, the more mobile primary magnet 36 is repelled away from less mobile secondary magnet 38. This repulsive force imparts a lifting moment to the device 196, preventing the tongue 34 from falling backward into the mouth and thereby avoiding an apneic or hypopneic event. In this arrangement, the direction of lift is upward and forward, as depicted by arrow 206 in FIG. 32, because the pivot point of arm 200 causes the path of travel to describe a radius centered on the upper rear corner of the bracket 198.

Figure 33:
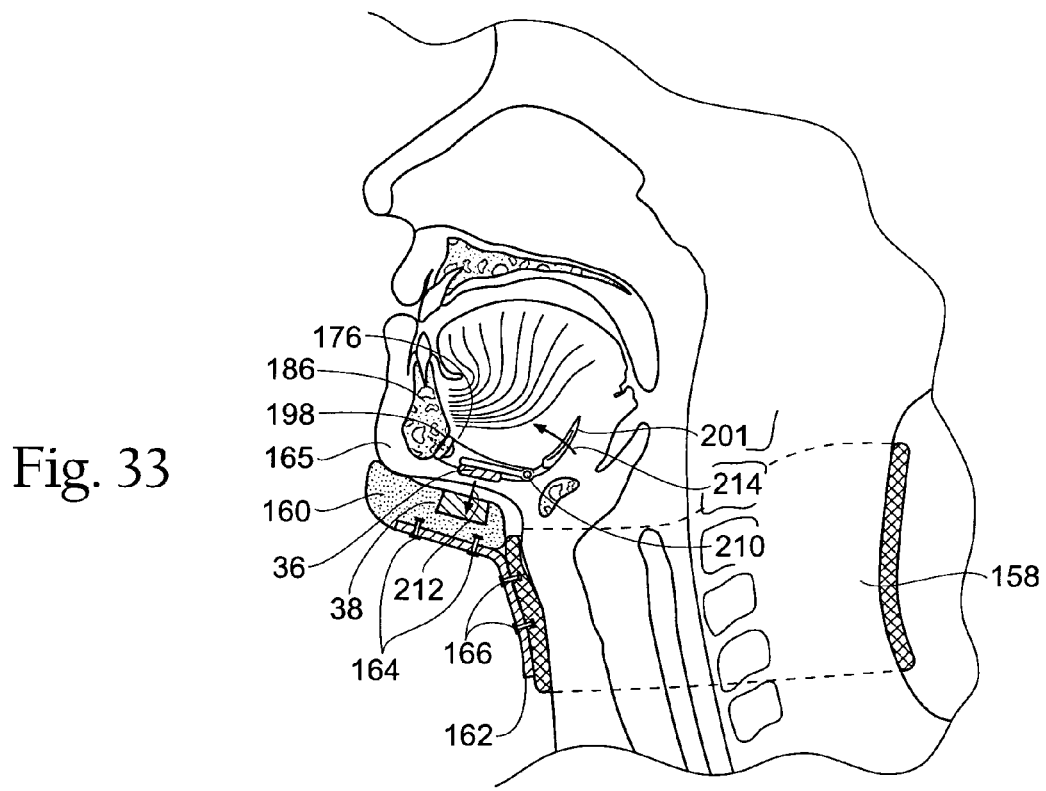
FIG. 33 is a side view of an alternative embodiment of the device shown in FIG. 32.
Figure 34:
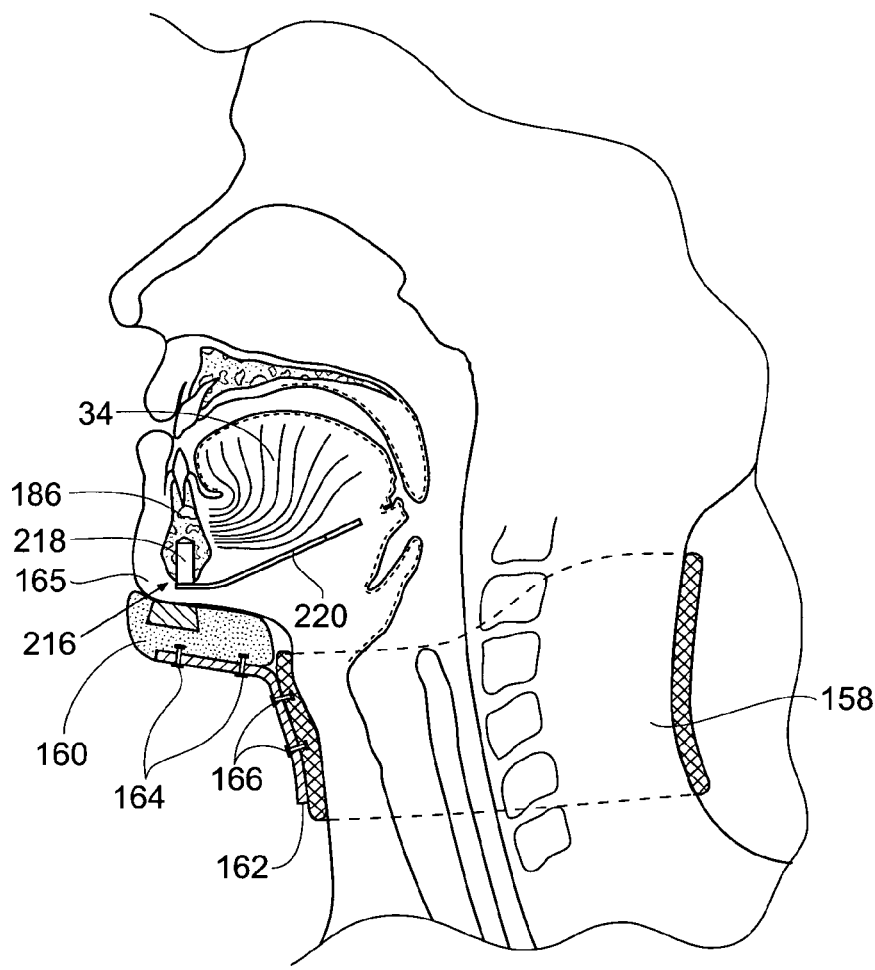
FIG. 34 is an anatomical cross-section of a human upper airway illustrating an alternative embodiment of the invention in which a primary magnet is carried by a device implanted into the mandible and a secondary magnet is carried by an external neck collar.
Figure 35:
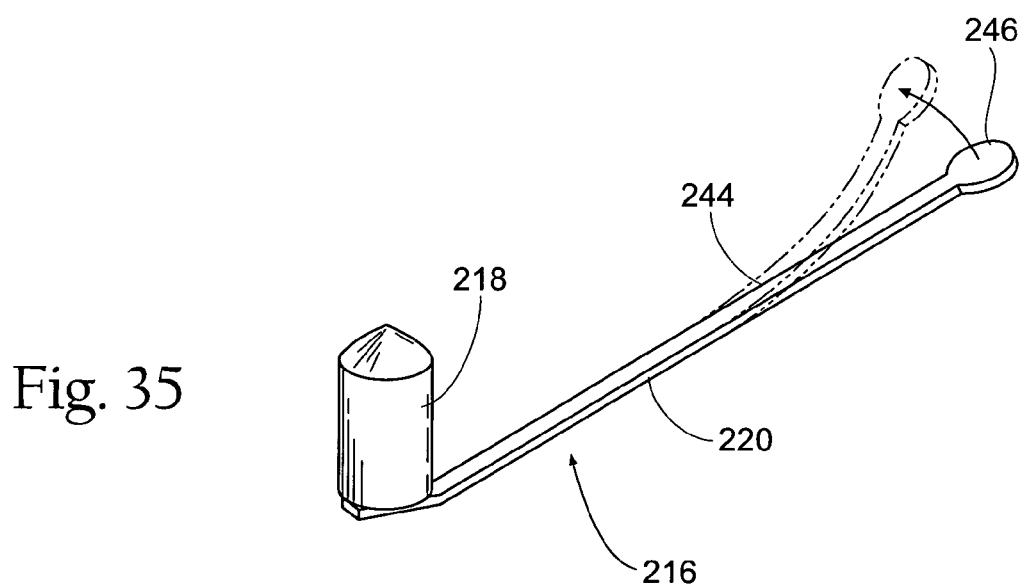
FIG. 35 is a perspective view of the device of FIG. 34 and illustrating upward movement of the lifting arm in response to anterior movement of the pull wire.

With reference now to FIG. 33, an alternative embodiment of the device 196 is illustrated. A bracket 198 is firmly affixed to the posterior surface of the mandible 186 using a bone screw 174. A bellcrank 208 is rotatably mounted to bracket 198, pivoting about a center point 210. A primary magnet 36 is affixed to the lower surface of the bellcrank 208 and positioned at the anterior end of the bellcrank 208.

For sleep, the user wears a collar apparatus 158 carrying a secondary magnet 38, as described earlier (see e.g., FIGS. 28 and 29). In this arrangement, the polarities of the primary and secondary magnets 36 and 38 are complentary, i.e., the polarities are not alike. Thus, the less mobile secondary magnet 38 will attract the more mobile primary magnet 36. The attraction imparts a downward pull, as depicted by arrow 212 in FIG. 33, on the anterior portion of the bellcrank 208. A downward force on the arm 200 at will translate to an arcuate force, represented by arrow 214 in FIG. 33, resisting the tendency of the tongue 34 to fall backward during sleep and attendant muscle relaxation.

The materials of construction of the device 168 or 196 are desirably of biologically inert materials that have demonstrated the ability to be implanted and remain within the body without causing irritation, inflammation or rejection by the body. Suitable materials are polymeric (plastic) materials or metallic materials such as titanium or shaped memory alloys. The moving or floating parts of the present invention are preferably made of materials that are somewhat flexible and that will not affect speech or swallowing during non-sleeping hours. The implanted portions of the device 168 or 196 may be of, or coated by, a material that promotes in growth or attachment of the tissue to the implanted device 168 or 196. Such materials are well known to the medical device industry.

It is believed that the restraint of the tongue 34 for treating sleep-related breathing disorders such as snoring, upper airway resistance syndrome and obstructive sleep apnea, does not require large forces. It is estimated that the required forces to be imparted to the device 168 or 196 when the collar 158 is worn are in the range of about 15 to 60 grams.

Thus, the lifting/rotating arms 178, 180 and 200 in the embodiments represented by FIGS. 30 to 33 could be composed of a metallic coil spring that is imbedded in a polymeric coating, such as PTFE (Teflon®), or a silicone rubber compound. The degree of flexibility and rigidity required to provide sufficient lifting force during sleep, while not interfering with normal daytime activities such as speech and swallowing, could be readily attained by varying the wire gage, number of turns and the type of covering material.

2. Second Embodiment

FIGS. 34 to 37 illustrate another embodiment of the invention in which a device 216 carrying a primary magnet 36 can be implanted within the mandible 186 for treating sleep-related breathing disorders such as snoring, upper airway resistance syndrome and obstructive sleep apnea. The device 216 comprises a capsule 218 coupled to a lifting arm 220. The capsule 218 includes a bore 222 in which the primary magnet 36 is positioned slidably and stabilized against the top end of the bore 222 by a light force coil spring 224. Below the magnet 36 is a linkage mechanism 226 on which the magnet 36 rests or, alternatively, is attached to.

The linkage mechanism 226 has a connecting rod 230 contacting the bottom surface of the magnet 36, which is coupled to a bellcrank 232, which pivots about a pivot point 228. The bellcrank 232 is coupled to the lifting arm 220 by a pull wire 236.

It is to be understood that the length of the arms of the bellcrank 232 on opposite sides of the pivot point 228 may dissimilar. For instance, the bellcrank arm above the pivot point 228 may be longer than the bellcrank arm below the pivot point 228 to gain a leverage advantage. In this arrangement, travel distance for the magnet 36 is traded for increased force at the end of the lower arm 232. These lengths may be designed to deliver the desired force at the end of the bellcrank 232 connected to the pull wire 236.

The proximal end of a pull wire 236 is attached to the bellcrank 232, e.g., threaded through hole 238 and tied. The wire 236 extends through a bore 240 in the lifting arm 220, the distal end of the wire 236 being anchored to the interior of the distal end of the lifting arm 220, e.g., threaded through hole 242 and tied. The lifting arm 220 includes a segmented portion 244, such that as the pull wire 236 is drawn back, the segmented portion 244 of the lifting arm 220 curves, as represented by arrow in FIG. 35. The arm 220 includes a paddle 246 at the posterior end that is configured to press in an anterior direction on the muscular tissue within the tongue 34 as the arm 220 curves.

The method of curving a hollow tube is well known in the medical device industry and is used for many types of steerable therapeutic and diagnostic devices, such as catheters and endoscopes. The exterior of the curvable lifting arm 220 is desirably coated with a material such as expanded PTFE to promote in growth of tissue and provide stability for the implanted lifting arm 220.

To implant the device 216, the surgeon performs a procedure to open the skin and tissue beneath the chin 165 to gain access to the lower surface of the mandible 186. The surgeon then drills a hole in the mandible 186 of an appropriate diameter and depth for the capsule 218 to be implanted.

The capsule 218 is then anchored into the mandible 186 using a bone cement of the type used in joint implants and similar procedures. Next, using a special procedure needle, the surgeon uses a locating template that temporarily attaches to the bottom of the capsule 218 to guide the procedure needle to create a path for the lifting arm 220. The surgeon then inserts the special needle, palpating the tongue 34 to determine the optimal location for the posterior of the lifting arm 220. The needle is then withdrawn and the sterile lifting arm 220 is slid into the incision made by the special needle. The anterior end of the lifting arm 220 includes an attachment means that will allow the lifting arm 220 end to be sealed to the bottom of the magnet capsule 218. The incision is then closed.

Figure 36:
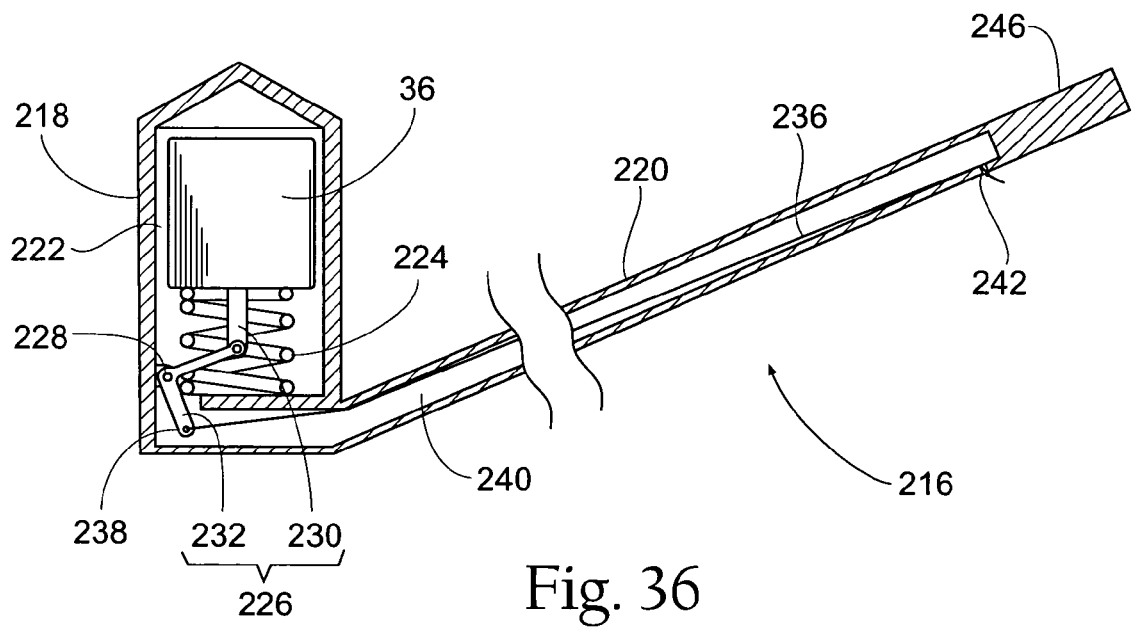
FIG. 36 is a cross-sectional view of the device of FIG. 35.
Figure 37:
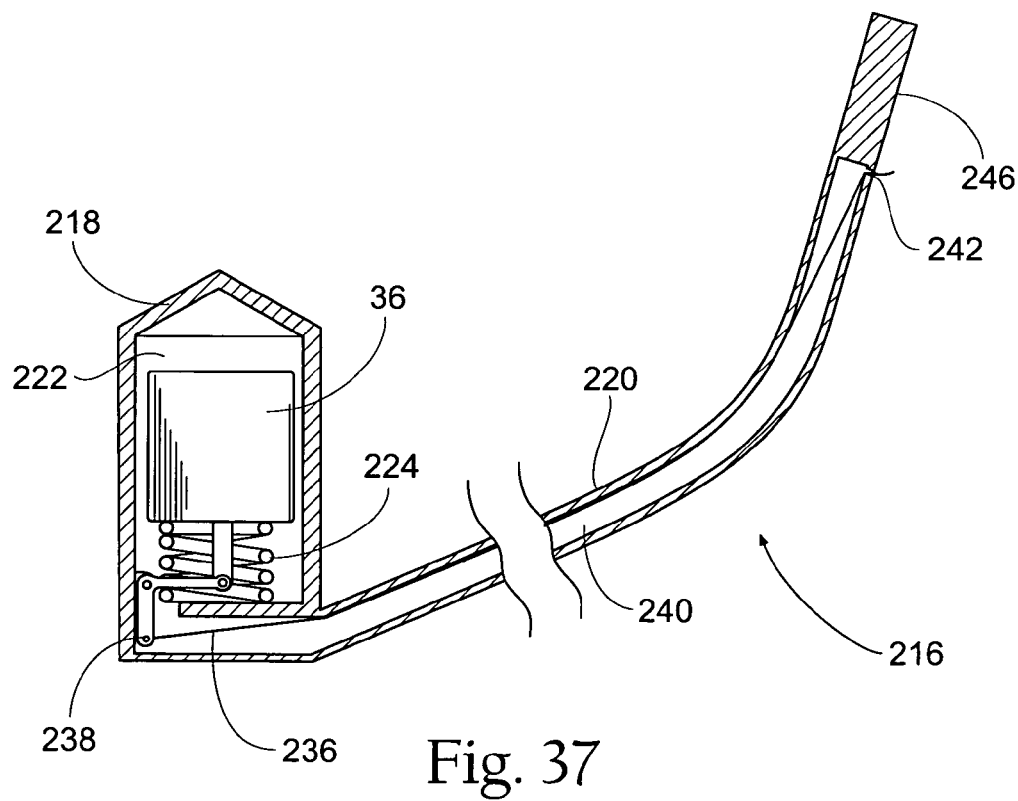
FIG. 37 is a view similar to FIG. 36 and illustrating the upward and forward movement of the lifting arm in response to the magnet being pulled in a downward direction.

After a suitable healing time to allow swelling and soreness to subside, the patient may begin to wear a collar 158 carrying the secondary magnet 38, similar to that shown in FIGS. 28 and 29. As best seen in FIG. 36, in the absence of magnetic forces acting on the primary magnet 36 (i.e., when the collar 158 is not being worn) the primary magnet 36 rests against the top end of the bore 222, as previously noted. When the collar 158 is worn, attractive magnetic forces between the complementary magnets 36 and 38 draw more the mobile primary magnet 36 to the bottom of the capsule 218, as shown in FIG. 37. The downward movement of magnet 36 results in the lower arm 232 pivoting in an upward direction to draw the pull wire 236 back (anterior).

As the wire 236 is drawn back, the segmented portion 244 of the lifting arm 220 curves upward to effectuate an upward and anterior movement of the tongue 34, mediating against OSA and hypopneas. Because the tongue 34 will not tend to occlude the airway, snoring that is exacerbated by a rearward tongue 34 position may also by reduced.

VI. Another System Overview (Tissue Displacement Using Suction)

FIGS. 38 to 41 illustrate another system 300 for treating sleep-related breathing disorders such as snoring, upper airway resistance syndrome and obstructive sleep apnea. Unlike the systems previously discussed, the system 300 does not employ magnets or ferrous materials. Instead, the system 300 uses suction (i.e., a vacuum) to position, stabilize and maintain a preferred orientation of tissue in an oral cavity and airway in both humans and animals. By using suction to move and stabilize tissue in a desired location and shape, the system 300 mediates or prevents the obstruction of the upper airway that results in sleep-related breathing disorders. And, as will be described, the system 300 achieves these results without permanent modification of the anatomy.

Figure 38:
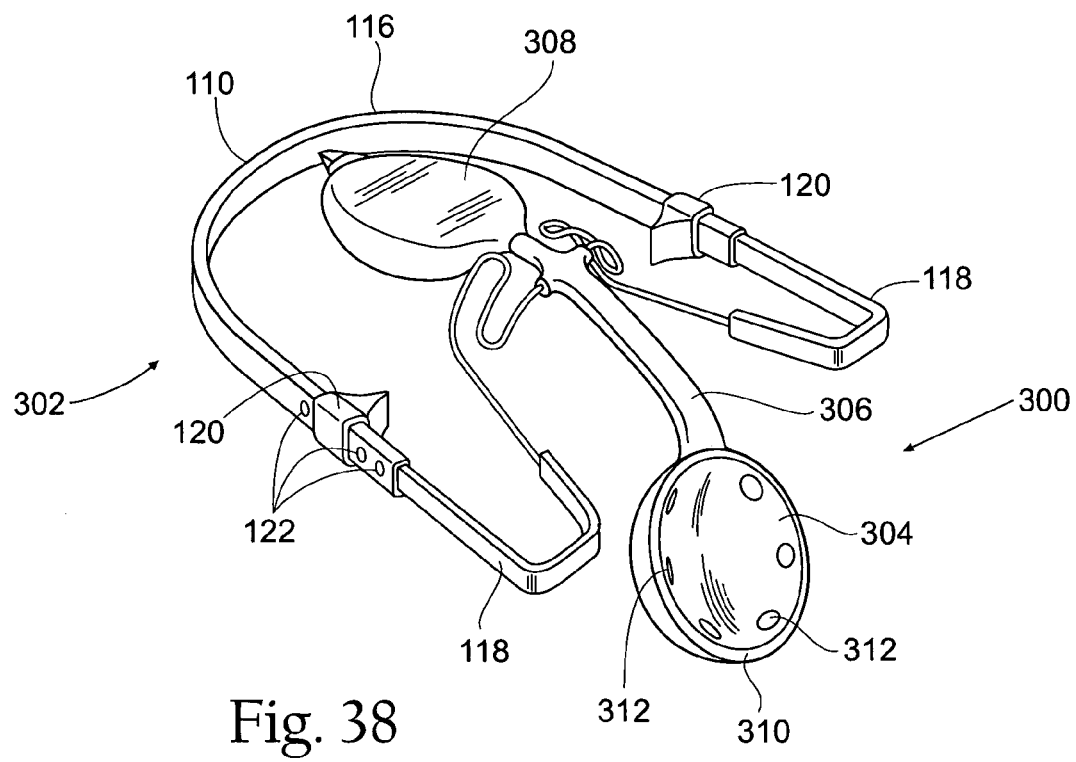
FIG. 38 is a perspective view of an oral appliance intended for placement within the oral cavity and including a suction source to affect anterior movement of the soft palate and/or uvula.
Figure 41:
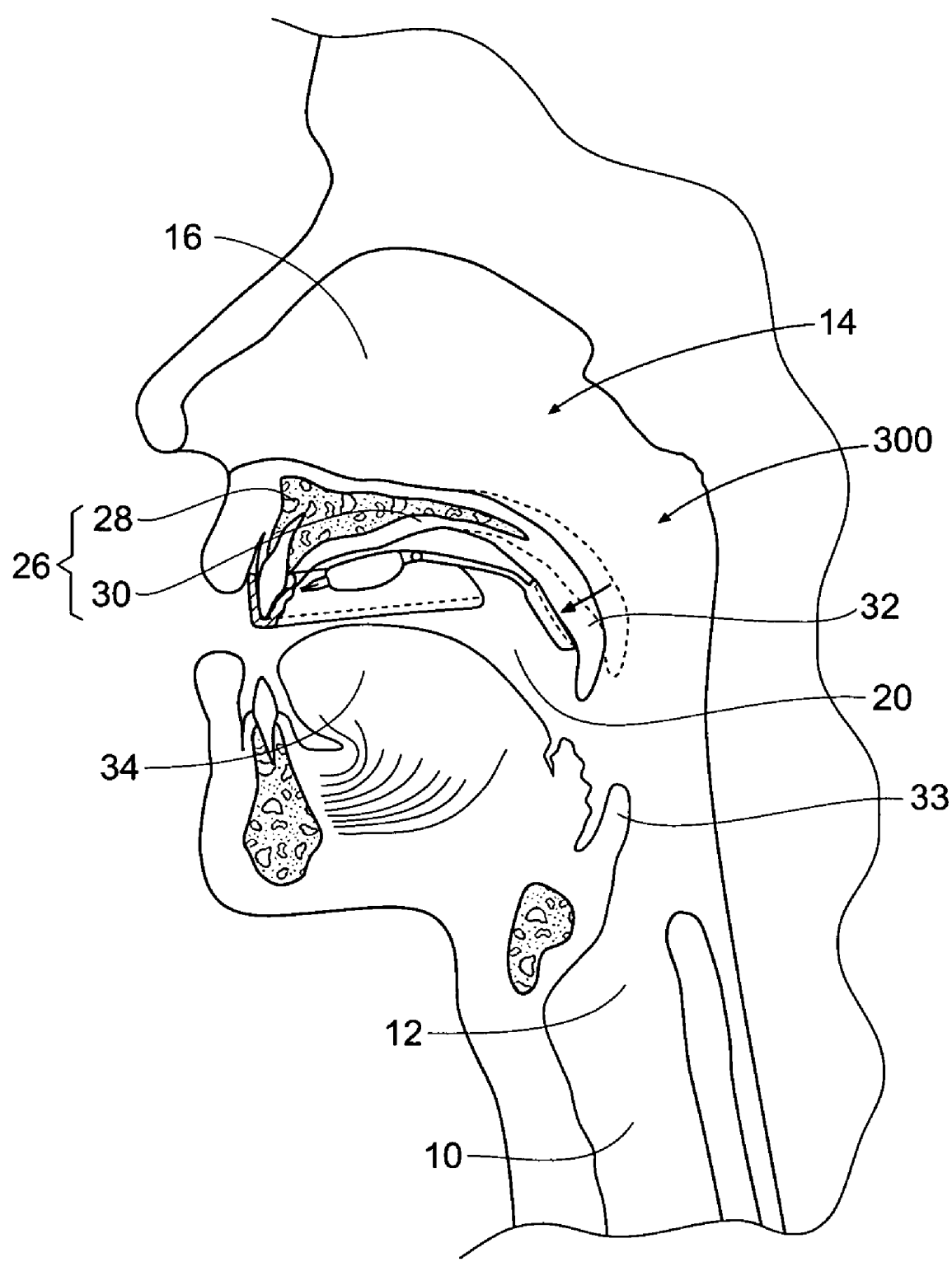
FIG. 41 is an anatomical view of a human oral cavity illustrating the placement of the oral appliance shown in FIG. 38 to affect anterior movement of the soft palate and/or uvula.

As shown in FIG. 38, the system 300 includes an oral device 302, which conforms to the teeth or hard palate (see FIG. 41). The oral device 302 has the structural features of oral device 104 shown in FIG. 18, which have been previously described and share common reference numerals. Like the oral device 104, the oral device 302 is held in place by an intimate fit to the teeth and/or hard palate 28 (as shown in FIG. 41) and/or by springs or elastic bands, all of which are well known and common in dental appliances. Like the oral device 104, the oral device 302 is intended to be worn by the individual during sleep and then removed during waking hours.

As shown in FIG. 38, the system 300 also includes a suction cup 304, a hollow supporting stem 306, and a vacuum bulb 308, which are carried by the oral device 302.

Figure 39:
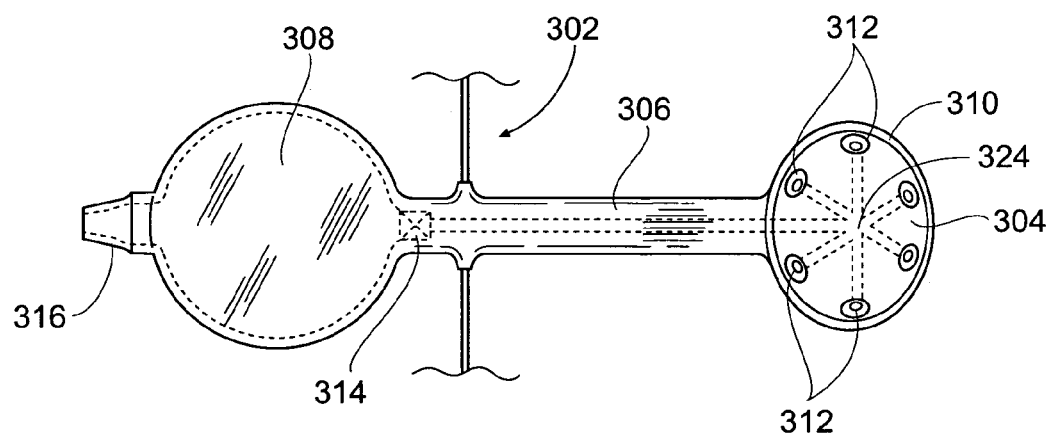
FIG. 39 is a top view of the suction source that is carried by the appliance shown in FIG. 38.

As FIGS. 38 and 39 show, the suction cup 304 desirably has a bead 310 which surrounds the face of the suction cup 304. The bead 310 is sized and configured to press against the surface of the tissue (see FIG. 40B), creating an area of increased contact pressure, resulting in a tight seal against the tissue. Perforations 312 in the face of the suction cup 304 reach into the plenum chamber 324 within the suction cup 304 (see FIG. 39). The face of the suction cup 304 which contacts the tissue may also have a shallow waffle type grid pattern to enhance evacuation of air from the area between the suction cup 304 and the surface of the tissue.

The stem 306 supports the suction cup 304. The stem 306 is hollow to transport air between the suction cup 304 and the vacuum bulb 308. The stem 306 is desirably flexible so that movement of the soft palate and uvula is not impaired, while imparting sufficient force to pull the soft palate and uvula in an anterior direction.

As FIG. 39 shows, the vacuum bulb 308 communicates with a check valve 314 and an exhaust valve 316. The body of the vacuum bulb 308 may be a flexible material with sufficient memory to expand after being depressed, creating suction forces, which are communicated via the hollow stem 306 to the suction cup 304.

Figure 40A:
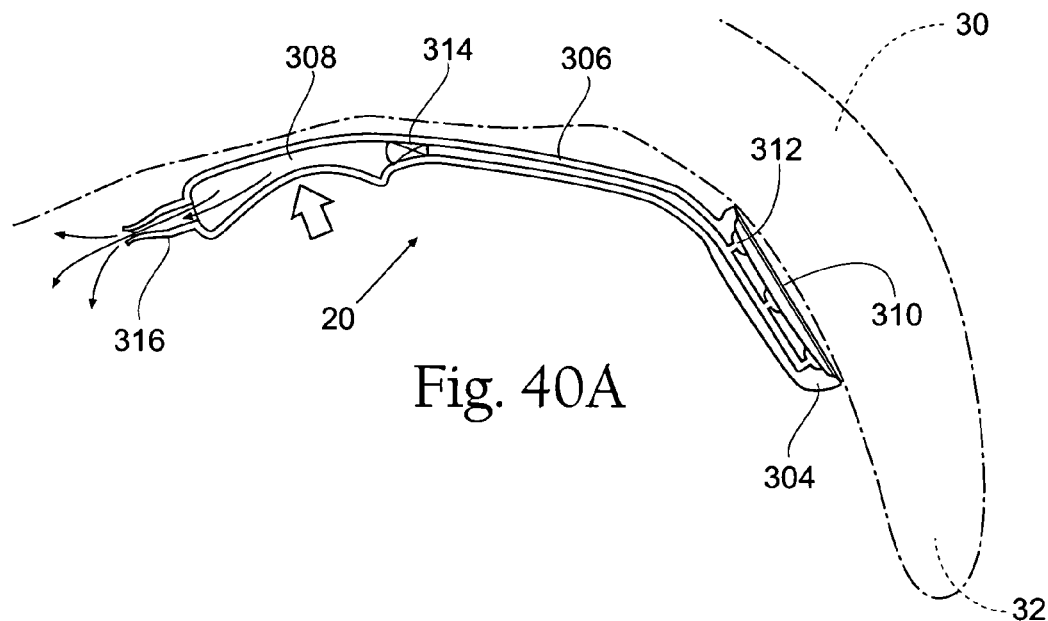
FIGS. 40A and 40B are side section views of the suction source shown in FIG. 39, being operated during use to affect anterior movement of the soft palate and/or uvula.

The bulb 308, the stem 306, and the suction cup 304 may be slidably mounted onto the oral device 302, in the manner that magnets were slidably affixed to the oral device 104 described earlier. In use (see FIG. 40A), the individual would slide the vacuum bulb 308 in a backward (posterior) direction in the mouth, causing the suction cup 304 to come into contact with the soft palate 30 and/or uvula 32. As FIG. 40A shows, the individual would then depress the vacuum bulb 308 by pressing upward (shown by an arrow in FIG. 40A). Air within the bulb 308 will exit through the exhaust valve 316 (shown by arrows in FIG. 40A), since air is unable to move toward the suction cup 304 because the check valve 314 prevents air movement in that direction.

Figure 40B:
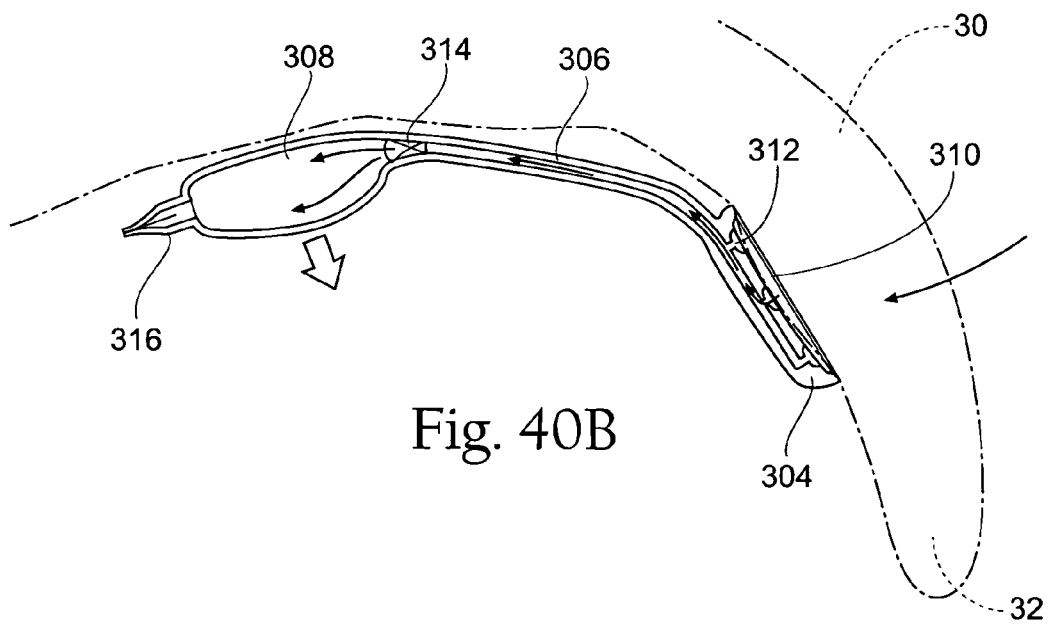

As FIG. 40B shows, when the pressure against the vacuum bulb 308 is released (shown by an arrow in FIG. 40B), the bulb 308 expands, reducing the internal pressure. This creates a suction in the suction cup 304, because the check valve 314 permits air movement toward the vacuum bulb 308 (as shown by an arrow in FIG. 40B). If desired, the individual may pump the suction cup 304 itself to further exhaust air, if needed, to assure an adequate suction grip on the tissue.

The exhaust valve 316 may be of a pressure limiting type of valve that will open if a predetermined amount of suction has been exceeded. Such a valve could have a calibrated spring to prevent maintaining an amount of suction that might result in tissue damage. If the vacuum bulb 308 was depressed more than required, the pressure regulating exhaust valve would leak until the predetermined level of suction was reached and then seal against further leakage.

The vacuum bulb 308 may be placed on the occlusal surfaces between upper and lower molars, allowing the suction to be created and replenished by a biting action. Alternatively, a primary suction bulb may be arranged as shown in FIGS. 38 and 39, and the amount of suction needed to overcome leakage may be supplied by a smaller occlusal bulb.

Various ancillary means may be applied to prevent leakage of the suction during the sleep period. For instance, a sealing gel material or dental adhesive might be applied to the bead of the suction cup, preventing air leakage during the night, in which case the suction applied when the device is placed in the mouth would be sufficient for the entire sleep period.

Figure 42:
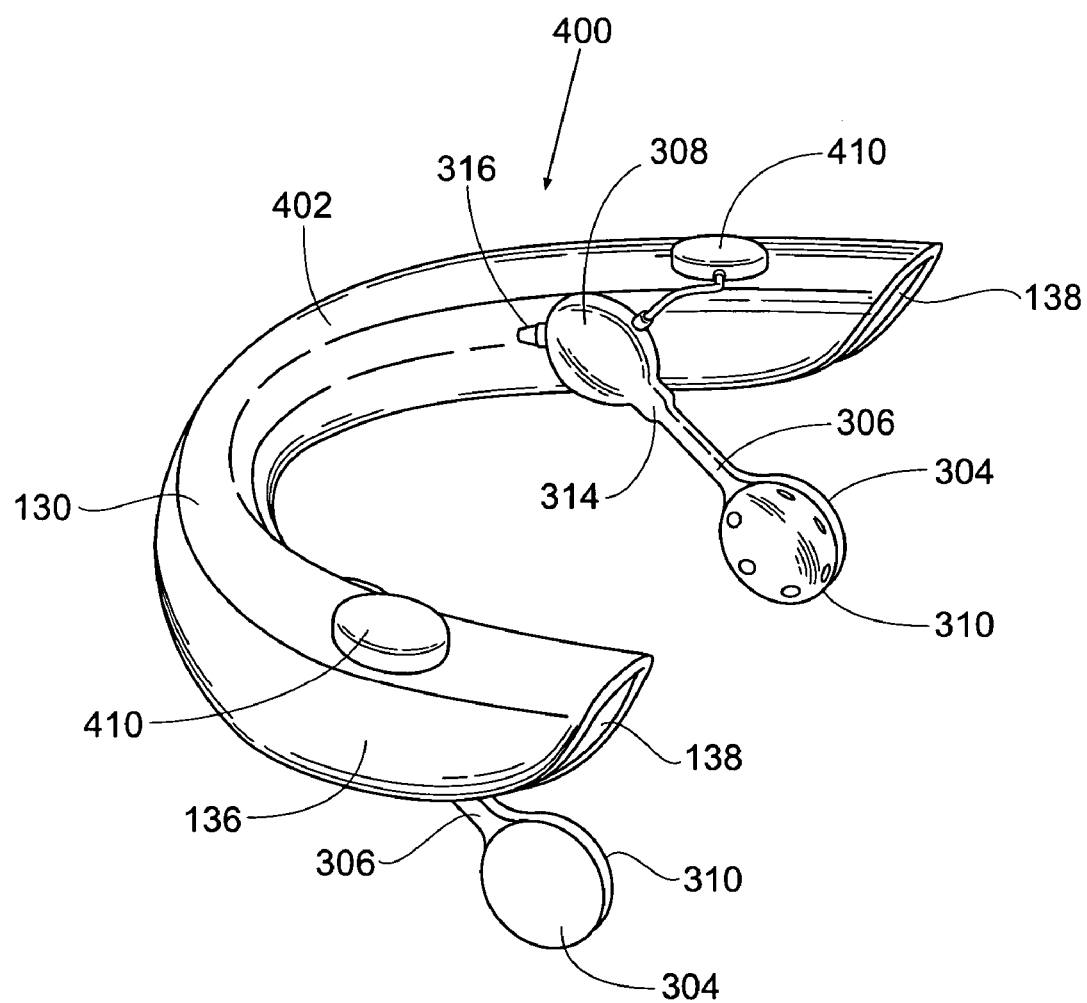
FIG. 42 is a perspective view of an oral appliance intended for placement on the bottom teeth within the oral cavity and including a suction source to affect anterior movement of the tongue.
Figure 43:
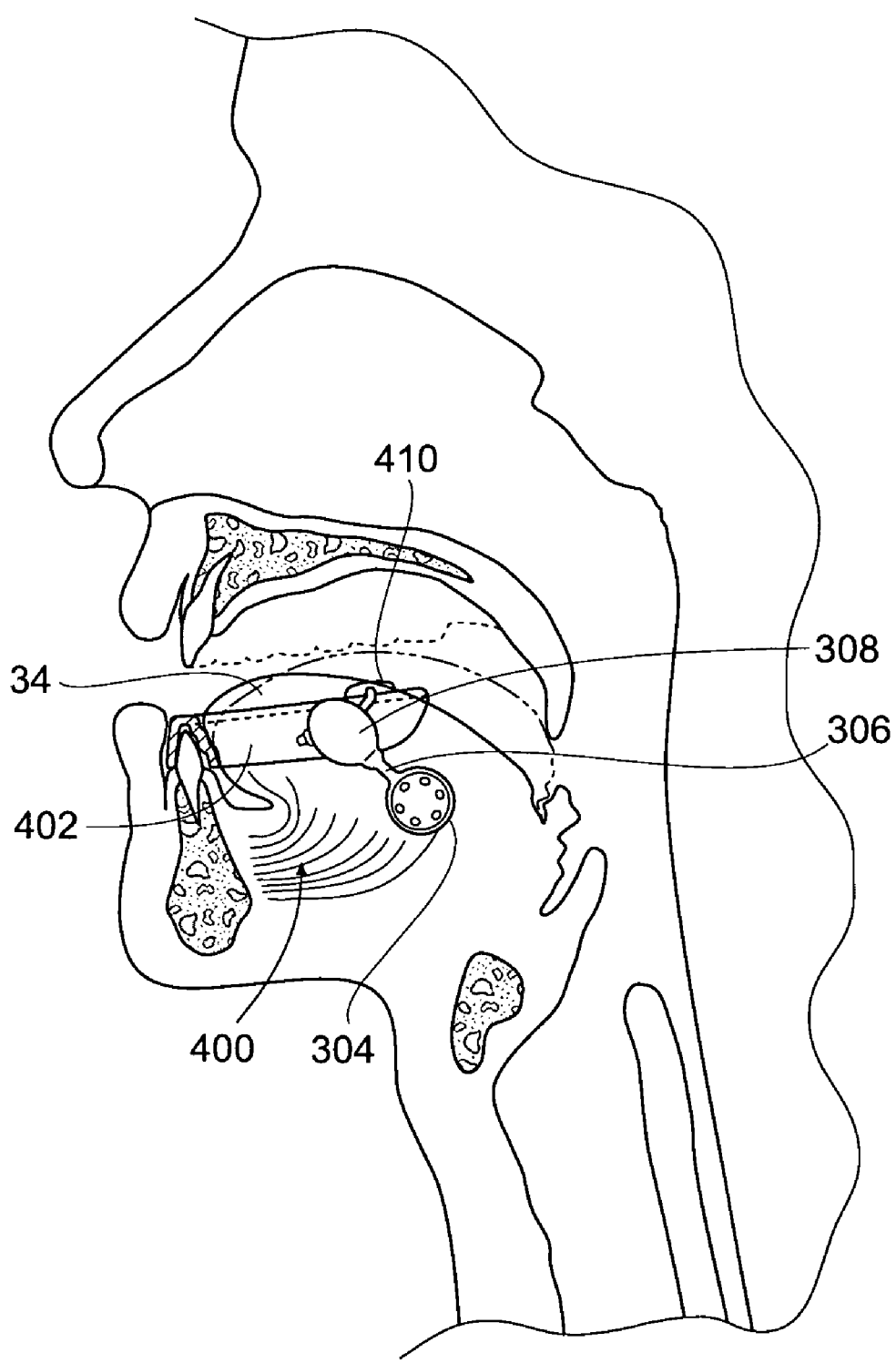
FIG. 43 is an anatomical view of a human oral cavity illustrating the placement of the oral appliance shown in FIG. 42 to affect anterior movement of the tongue.

FIGS. 42 and 43 illustrate an alternative system 400 for treating sleep-related breathing disorders such as snoring, upper airway resistance syndrome and obstructive sleep apnea. The system 400, like the system 300 uses suction (i.e., a vacuum) to position, stabilize and maintain a preferred orientation of tissue in an oral cavity and airway in both humans and animals. More particularly, the system 400 applies suction to stabilize and maintain the tongue 34 in a preferred orientation in the oral cavity and airway. The benefits of maintaining the tongue 34 in a preferred orientation using primary and secondary magnets have been previously described, and the use of suction achieves comparable benefits.

As shown in FIG. 42, the system 400 includes an oral device 402, which can be sized and configured to be carried by either the bottom or upper teeth. In FIG. 42, the oral device 402 is sized and configured to be carried by the bottom teeth and has the structural features of oral device 126 shown in FIG. 22, which have been previously described and, accordingly, share common reference numerals. Like the oral device 126, the oral device 402 is held in place by an intimate fit to the bottom teeth. Like the oral device 126, the oral device 402 is intended to be worn by the individual during sleep and then removed during waking hours.

As also shown in FIG. 42, the system 400 also includes a left and right pair of suction cups 304 carried by the oral device 402. Each suction cup 304 has a hollow supporting stem 306 and a vacuum bulb 308, which are also carried by the oral device 402. These elements are comparable in structure and function to the elements 304, 306, and 308 shown and described in the embodiment illustrated in FIGS. 38 and 39 and are, accordingly, assigned the same reference numeral.

As in the embodiment shown in FIGS. 38 and 39, the suction cups 304 in FIG. 42 desirably each has a bead 310 that is sized and configured to press against the adjacent tissue, which, in this instance, is a side surface of the tongue 34 (see FIG. 43). As in the FIG. 39 embodiment, the vacuum bulb 308 in FIG. 42 communicates with a check valve 314 and an exhaust valve 316, to create suction in the respective suction cup 304 in response to an individual squeezing the vacuum bulb 308.

In use (see FIG. 43), the individual installs the oral device 402 on the bottom teeth. This installation brings the left and right suction cups 304 into association with the adjacent left and right sides of the tongue 34. The individual then depresses the vacuum bulbs 308 by pressing against them, either individually or simultaneously. When the pressure against the respective vacuum bulb 308 is released, the bulb 308 expands to create a suction in the associated suction cup 304. This has been previously described with reference to FIGS. 40A and 40B. In FIG. 43, the suction causes the suction cups 34 to grip the sides of the tongue 34.

The suction cups 304 are maintained by the oral device 402 in a desired anterior position within the oral cavity. Held relatively immobile by the bottom teeth, the suction cups 304 exert an anterior pulling force to the tongue 34. The pulling force draws the tongue toward a more forward, stabilized position, shown in solid lines in FIG. 43. The anterior position of the tongue 34 shown in FIG. 43 is comparable to the anterior position affected by the magnets 36'/38' shown in FIG. 23. The stabilization of the tongue 34 in an anterior direction prevents a potential obstruction of the airway (which is shown in phantom lines in FIG. 43).

As before described, one or more smaller, secondary vacuum bulbs 410 can be located on the oral device 402 in the occlusal area between upper and lower molars (see FIG. 42). The vacuum bulbs 410 are coupled to the suction cups 304 and apply suction to the cups 304 by biting action. In this arrangement, primary suction can be supplied by the main vacuum bulbs 308, and maintenance suction can be applied by biting on the secondary vacuum bulbs 410.

Alternatively, one or more suction cups 304 for gripping the sides of the tongue, along with the associated stems 306 and vacuum bulbs 308, can be carried by an oral device carried by the upper teeth, in a manner comparable to the way the magnets 132 are carried by the oral device 152 in FIG. 27.

The above described embodiments of this invention are merely descriptive of its principles and are not to be limited. The scope of this invention instead shall be determined from the scope of the following claims, including their equivalents.

What is claimed is:

1. An implant assembly comprising
   a first implant element sized and configured for implantation in a mandible within an oral cavity,
   a second implant element sized and configured for implantation in a tongue region within the oral cavity, and
   a third implant element coupled to the first and second implant elements within the oral cavity, the third implant element being capable of applying force between the first and second implant elements such that the implant, in use, resists posterior movement of the tongue within the oral cavity.

2. An implant assembly according to claim 1 wherein the third implant element includes an elongated member that applies the force.

3. An implant assembly according to claim 1 wherein the third implant element includes an elongated member that pulls the second implant element toward the first implant element.

4. An implant assembly according to claim 1 wherein the third implant element includes an elongated member that applies tension between the first and second implant elements.

5. An implant assembly comprising
   a first implant element sized and configured for implantation in a hyoid bone within an oral cavity,
   a second implant element sized and configured for implantation in a tongue region within the oral cavity, and
   a third implant element coupled to the first and second implant elements within the oral cavity, the third implant element being capable of applying force between the first and second implant elements such that the implant, in use, resists posterior movement of the tongue within the oral cavity.

6. An implant assembly according to claim 1 or 5 wherein the third implant element includes a component that applies force between the first and second implant elements in response to magnetic interaction with another component.

7. An implant assembly according to claim 1 or 5 wherein the second implant element pivots relative to the first implant element in response to the force applied by the third implant element.

8. An implant assembly comprising a first implant element sized and configured for implantation in a mandible within an oral cavity, a second implant element sized and configured for implantation in a tongue region within the oral cavity, and a third implant element coupled to the first and second implant elements within the oral cavity, the third implant element being capable of applying tension between the first and second implant elements such that the implant, in use, resists posterior movement of the tongue within the oral cavity.

9. An implant assembly according to claim 8 wherein the third implant element includes a component that applies tension between the first and second implant elements in response to magnetic interaction with another component.

10. An implant assembly according to claim 8 wherein the third implant element includes an elongated member.

11. A method comprising implanting a first implant element in a mandible within an oral cavity, implanting a second implant element in a tongue region within the oral cavity, and resisting posterior movement of the tongue within the oral cavity by coupling the first implant element to the second implant element within the oral cavity.

12. A method comprising implanting a first implant element in a hyoid bone within an oral cavity, implanting a second implant element in a tongue region within the oral cavity, and resisting posterior movement of the tongue within the oral cavity by coupling the first implant element to the second implant element within the oral cavity.

13. A method according to claim 11 or 12 wherein resisting posterior movement of the tongue within the oral cavity includes a generation of a magnetic field affecting the first and second implant elements.

14. A method comprising implanting a first implant element in a mandible within an oral cavity, implanting a second implant element in a tongue region within the oral cavity, and resisting posterior movement of the tongue within the oral cavity by placing into tension a third implant element between the second implant element and the first implant element within the oral cavity.

15. A method according to claim 14 wherein the third element comprises an elongated member placed into tension between the first and second implant elements.

16. A method according to claim 14 wherein by placing into tension a third implant element between the second implant element and the first implant element includes a generation of a magnetic field.

* * * * *